(12) United States Patent
Wadley et al.

(10) Patent No.: US 10,032,223 B2
(45) Date of Patent: *Jul. 24, 2018

(54) SYSTEM FOR ACCOUNT LINKING AND FUTURE EVENT INTEGRATION INTO RETIREMENT SCORE CALCULATION

(71) Applicant: BANK OF AMERICA CORPORATION, Charlotte, NC (US)

(72) Inventors: Cameron Darnell Wadley, Waxhaw, NC (US); Katherine Dintenfass, Charlotte, NC (US); Daralyn Marie Nicholson, Charlotte, NC (US); Carrie Anne Hanson, Charlotte, NC (US)

(73) Assignee: Bank of America Corporation, Charlotte, NC (US)

( * ) Notice: Subject to any disclaimer, the term of this patent is extended or adjusted under 35 U.S.C. 154(b) by 510 days.

This patent is subject to a terminal disclaimer.

(21) Appl. No.: 14/664,473

(22) Filed: Mar. 20, 2015

(65) Prior Publication Data

US 2016/0275612 A1  Sep. 22, 2016

(51) Int. Cl.
G06Q 40/06 (2012.01)
G06Q 40/08 (2012.01)
G16H 50/30 (2018.01)

(52) U.S. Cl.
CPC .............. *G06Q 40/06* (2013.01); *G06Q 40/08* (2013.01); *G16H 50/30* (2018.01)

(58) Field of Classification Search
CPC ......... G06Q 40/06; G06Q 40/08; G16H 50/30
USPC .............................................. 705/36, 36 R, 4
See application file for complete search history.

(56) References Cited

U.S. PATENT DOCUMENTS

| | | |
|---|---|---|
| 3,015,090 A | 12/1961 | Landauer |
| 3,050,095 A | 8/1962 | Prather |
| 5,253,192 A | 10/1993 | Tufts |
| 5,341,063 A | 8/1994 | Kumar |

(Continued)

OTHER PUBLICATIONS

Routine Exercise Found to Extend Life Almost Five Years. (Nov. 8, 2012). States News Service Retrieved from https://dialog.proquest.com/professional/docview/1149682410?accountid=142257 retrieved on Mar. 2, 2018 (Year: 2012).*

(Continued)

*Primary Examiner* — Kito R Robinson
(74) *Attorney, Agent, or Firm* — Michael A. Springs; Moore & Van Allen PLLC; Peter B. Stewart

(57) ABSTRACT

Embodiments of the invention are directed to systems, methods, and computer program products for assessing retirement planning based on a retirement score. The system is configured to compile projected retirement information of a first user, wherein the retirement information comprises a user profile of the first user. Based on the user profile of the first user, the system generates a projected retirement score. After generating the projected retirement score, the system receives a request to link a user profile for a second user to the user profile of the first user. The system projected retirement information of the second user and combines the projected retirement information of the first user with the projected retirement information of the second user, thus resulting in combined projected retirement information. Using both the projected retirement information, the system updates the projected retirement score.

20 Claims, 14 Drawing Sheets

(56) References Cited

U.S. PATENT DOCUMENTS

| | | |
|---|---|---|
| 5,430,542 A | 7/1995 | Shepherd |
| 5,471,575 A | 11/1995 | Giansante |
| 5,684,190 A | 11/1997 | Fechter et al. |
| 5,799,287 A | 8/1998 | Dembo |
| 5,920,848 A | 7/1999 | Schutzer et al. |
| 5,937,387 A * | 8/1999 | Summerell ......... G06F 19/3456 705/2 |
| 5,987,433 A | 11/1999 | Crapo |
| 6,086,768 A | 7/2000 | Sims et al. |
| 6,253,192 B1 | 6/2001 | Corlett et al. |
| 6,430,542 B1 | 8/2002 | Moran |
| 6,585,622 B1 | 7/2003 | Shum et al. |
| 6,601,044 B1 | 7/2003 | Wallman |
| 6,625,582 B2 | 9/2003 | Richman et al. |
| 6,684,190 B1 | 1/2004 | Powers et al. |
| 6,985,880 B1 | 1/2006 | Hodgdon et al. |
| 6,996,539 B1 | 2/2006 | Wallman |
| 7,171,384 B1 | 1/2007 | Fitzpatrick et al. |
| 7,174,313 B1 | 2/2007 | Martinez |
| 7,216,099 B2 | 5/2007 | Chen et al. |
| 7,296,734 B2 | 11/2007 | Pliha |
| 7,313,540 B1 | 12/2007 | Hueler et al. |
| 7,340,433 B1 | 3/2008 | Kay et al. |
| 7,340,534 B2 | 3/2008 | Cameron et al. |
| 7,373,324 B1 | 5/2008 | Engin et al. |
| 7,421,407 B2 | 9/2008 | Long, III et al. |
| 7,454,379 B1 | 11/2008 | Wolzenski et al. |
| 7,490,050 B2 | 2/2009 | Grover et al. |
| 7,577,597 B1 | 8/2009 | Allison et al. |
| 7,627,512 B2 | 12/2009 | Harris et al. |
| 7,630,986 B1 | 12/2009 | Herz et al. |
| 7,634,436 B1 | 12/2009 | Wagner |
| 7,647,261 B2 | 1/2010 | Merton et al. |
| 7,668,764 B2 | 2/2010 | Wilson |
| 7,725,387 B1 | 5/2010 | Fitch et al. |
| 7,774,324 B1 | 8/2010 | Henderson |
| 7,783,545 B2 | 8/2010 | Sloan et al. |
| 7,822,654 B2 | 10/2010 | Block et al. |
| 7,840,428 B2 | 11/2010 | McNab et al. |
| 7,840,463 B1 | 11/2010 | Davis |
| 7,840,470 B2 * | 11/2010 | Robinson ............... G06Q 40/00 705/36 R |
| 7,895,102 B1 | 2/2011 | Wilks et al. |
| 7,962,389 B1 | 6/2011 | Pilato |
| 7,970,684 B1 | 6/2011 | Benda |
| 7,979,335 B2 | 7/2011 | Schneider |
| 8,005,740 B2 | 8/2011 | Arnott et al. |
| 8,015,090 B1 | 9/2011 | Borzych et al. |
| 8,050,095 B2 | 11/2011 | Gonzalez et al. |
| 8,050,995 B1 | 11/2011 | Landry et al. |
| 8,069,103 B1 | 11/2011 | Davis |
| 8,099,361 B1 | 1/2012 | Gupta et al. |
| 8,112,331 B2 | 2/2012 | Getty |
| 8,121,915 B1 | 2/2012 | Igoe et al. |
| 8,175,971 B1 | 5/2012 | Landry |
| 8,180,695 B2 | 5/2012 | Ameriks et al. |
| 8,185,463 B1 | 5/2012 | Ball |
| 8,229,850 B2 | 7/2012 | Dilip et al. |
| 8,239,298 B1 | 8/2012 | Wilson et al. |
| 8,255,308 B2 | 8/2012 | Dial et al. |
| 8,280,798 B1 | 10/2012 | Benda |
| 8,290,860 B1 | 10/2012 | Bent et al. |
| 8,326,728 B1 | 12/2012 | Devaney et al. |
| 8,332,297 B1 | 12/2012 | Claus et al. |
| 8,341,063 B1 | 12/2012 | Cernyar |
| 8,346,647 B1 | 1/2013 | Phelps et al. |
| 8,354,933 B2 | 1/2013 | Bresch et al. |
| 8,370,179 B2 | 2/2013 | Foley et al. |
| 8,387,874 B1 | 3/2013 | Bohen et al. |
| 8,412,624 B2 | 4/2013 | Scherpa et al. |
| 8,417,608 B2 | 4/2013 | Benefield et al. |
| 8,428,974 B2 | 4/2013 | Oliver |
| 8,429,051 B1 | 4/2013 | Samson |
| 8,446,275 B2 | 5/2013 | Utter |
| 8,484,109 B1 | 7/2013 | Nelson Deurmier et al. |
| 8,527,382 B2 | 9/2013 | McDonough et al. |
| 8,533,092 B1 | 9/2013 | Burrow et al. |
| 8,571,984 B1 | 10/2013 | Bent et al. |
| 8,595,105 B2 | 11/2013 | Hirsch |
| 8,606,678 B2 | 12/2013 | Jackowitz et al. |
| 8,635,132 B1 | 1/2014 | Wilks et al. |
| 8,650,110 B2 | 2/2014 | Green |
| 8,676,687 B2 | 3/2014 | McDonough et al. |
| 8,682,698 B2 | 3/2014 | Cashman et al. |
| 8,688,556 B2 | 4/2014 | Greene et al. |
| 8,688,557 B2 | 4/2014 | Rose et al. |
| 8,688,558 B2 | 4/2014 | Chadwick |
| 8,688,575 B2 | 4/2014 | Steiner |
| 8,706,590 B2 | 4/2014 | Benefield et al. |
| 8,751,345 B1 | 6/2014 | Borzych et al. |
| 8,751,356 B1 | 6/2014 | Garcia |
| 8,768,800 B2 | 7/2014 | Erla et al. |
| 8,781,929 B2 | 7/2014 | Stiff et al. |
| 8,930,217 B2 | 1/2015 | Feinschreiber et al. |
| 8,930,228 B1 | 1/2015 | Ball |
| 9,105,145 B2 | 8/2015 | Brown et al. |
| 9,727,885 B1 | 8/2017 | Reier |
| 9,830,660 B2 | 11/2017 | Dintenfass et al. |
| 2001/0009003 A1 | 7/2001 | Groat et al. |
| 2001/0009004 A1 | 7/2001 | Groat et al. |
| 2001/0037276 A1 | 11/2001 | Kelly et al. |
| 2001/0042037 A1 | 11/2001 | Kam et al. |
| 2001/0025309 A1 | 12/2001 | Beck et al. |
| 2002/0035527 A1 | 3/2002 | Corrin |
| 2002/0069090 A1 | 6/2002 | De Grosz et al. |
| 2002/0077946 A1 | 6/2002 | Caplan et al. |
| 2002/0091608 A1 | 7/2002 | Odegaard et al. |
| 2002/0111890 A1 | 8/2002 | Sloan et al. |
| 2002/0133368 A1 | 9/2002 | Strutt et al. |
| 2002/0198801 A1 | 12/2002 | Dixon et al. |
| 2003/0050883 A1 | 3/2003 | Weir et al. |
| 2003/0172018 A1 | 9/2003 | Chen et al. |
| 2003/0177044 A1 | 9/2003 | Sokel et al. |
| 2003/0191705 A1 | 10/2003 | Miyata et al. |
| 2003/0208432 A1 | 11/2003 | Wallman |
| 2003/0233301 A1 | 12/2003 | Chen et al. |
| 2004/0030589 A1 | 2/2004 | Leisher et al. |
| 2004/0054610 A1 | 3/2004 | Amstutz et al. |
| 2004/0059627 A1 | 3/2004 | Baseman et al. |
| 2004/0111370 A1 | 6/2004 | Saylors et al. |
| 2004/0138983 A1 | 7/2004 | Nishimaki |
| 2004/0177022 A1 | 9/2004 | Williams et al. |
| 2004/0205008 A1 | 10/2004 | Haynie et al. |
| 2005/0080725 A1 | 4/2005 | Pick |
| 2005/0097033 A1 | 5/2005 | Pretell et al. |
| 2005/0125338 A1 | 6/2005 | Tidwell et al. |
| 2005/0149436 A1 | 7/2005 | Elterich |
| 2005/0267816 A1 | 12/2005 | Jaramillo |
| 2005/0289045 A1 | 12/2005 | Lawson |
| 2006/0074788 A1 | 4/2006 | Grizack et al. |
| 2006/0106698 A1 | 5/2006 | Mahaney et al. |
| 2006/0155639 A1 | 7/2006 | Lynch et al. |
| 2006/0212380 A1 | 9/2006 | Williams et al. |
| 2006/0218103 A1 | 9/2006 | Williams |
| 2006/0241859 A1 | 10/2006 | Kimchi et al. |
| 2006/0253360 A1 | 11/2006 | Gould |
| 2006/0271463 A1 | 11/2006 | Young |
| 2007/0011063 A1 | 1/2007 | Shelon et al. |
| 2007/0027736 A1 | 2/2007 | Reynolds et al. |
| 2007/0038522 A1 | 2/2007 | Bell et al. |
| 2007/0038544 A1 | 2/2007 | Snow et al. |
| 2007/0106589 A1 | 5/2007 | Schirripa |
| 2007/0192457 A1 | 8/2007 | Ervin |
| 2007/0239572 A1 | 10/2007 | Harris et al. |
| 2007/0244780 A1 | 10/2007 | Liu |
| 2007/0250427 A1 | 10/2007 | Robinson |
| 2007/0271201 A1 | 11/2007 | Armand et al. |
| 2007/0288399 A1 | 12/2007 | Reynolds et al. |
| 2008/0091459 A1 | 4/2008 | Elgar et al. |
| 2008/0171584 A1 * | 7/2008 | Roberts ................ A63F 13/10 463/9 |
| 2008/0195542 A1 | 8/2008 | Al Zarawani |
| 2008/0220230 A1 | 8/2008 | Hardison |
| 2008/0215500 A1 | 9/2008 | De La Motte |

(56) References Cited

U.S. PATENT DOCUMENTS

| | | | |
|---|---|---|---|
| 2008/0270304 A1 | 10/2008 | Brown | |
| 2008/0288416 A1 | 11/2008 | Arnott et al. | |
| 2009/0006251 A1 | 1/2009 | Haase et al. | |
| 2009/0024540 A1 | 1/2009 | Ryder | |
| 2009/0030853 A1 | 1/2009 | De La Motte | |
| 2009/0037226 A1* | 2/2009 | Radin | G06Q 10/10 705/4 |
| 2009/0055327 A1 | 2/2009 | Jones et al. | |
| 2009/0063310 A1 | 3/2009 | Alonzo et al. | |
| 2009/0106136 A1 | 4/2009 | Wright | |
| 2009/0157811 A1 | 6/2009 | Bailor et al. | |
| 2009/0171842 A1 | 7/2009 | Blythe | |
| 2009/0281959 A1 | 11/2009 | Abidi et al. | |
| 2009/0319438 A1* | 12/2009 | Jain | G06Q 40/00 705/36 R |
| 2009/0327155 A1 | 12/2009 | Dial et al. | |
| 2010/0017342 A1 | 1/2010 | Boscaljon | |
| 2010/0030686 A1 | 2/2010 | Lee et al. | |
| 2010/0046871 A1 | 2/2010 | Norimatsu et al. | |
| 2010/0094740 A1 | 4/2010 | Richter | |
| 2010/0094778 A1 | 4/2010 | Wagner | |
| 2010/0100470 A1 | 4/2010 | Buchanan et al. | |
| 2010/0125535 A1 | 5/2010 | Nowak et al. | |
| 2010/0131424 A1 | 5/2010 | Mose et al. | |
| 2010/0153138 A1 | 6/2010 | Evans | |
| 2010/0161467 A1 | 6/2010 | Ageenko et al. | |
| 2010/0179920 A1 | 7/2010 | Snodgrass | |
| 2010/0223072 A1 | 9/2010 | Jacobson | |
| 2010/0228651 A1 | 9/2010 | Becerra et al. | |
| 2010/0268670 A1 | 10/2010 | Dahlberg et al. | |
| 2011/0047070 A1 | 2/2011 | Farias | |
| 2011/0047093 A1 | 2/2011 | Faust | |
| 2011/0054948 A1 | 3/2011 | Gopi et al. | |
| 2011/0106691 A1 | 5/2011 | Clark et al. | |
| 2011/0112985 A1 | 5/2011 | Kocmond | |
| 2011/0145166 A1 | 6/2011 | Kmak et al. | |
| 2011/0166978 A1 | 7/2011 | Mastrogiovanni | |
| 2011/0166987 A1 | 7/2011 | Hu et al. | |
| 2011/0178910 A1 | 7/2011 | Benefield et al. | |
| 2011/0251978 A1 | 10/2011 | Davies et al. | |
| 2012/0072572 A1 | 3/2012 | Bladel | |
| 2012/0150769 A1 | 6/2012 | Frank | |
| 2012/0215716 A1 | 8/2012 | Shier, Jr. et al. | |
| 2012/0239416 A1 | 9/2012 | Langva | |
| 2012/0246045 A1 | 9/2012 | Hirsch | |
| 2012/0259797 A1 | 10/2012 | Sarkany et al. | |
| 2012/0310677 A1 | 12/2012 | Calibey et al. | |
| 2012/0317016 A1* | 12/2012 | Hughes | G06Q 40/025 705/38 |
| 2012/0330687 A1 | 12/2012 | Hilario et al. | |
| 2013/0013478 A1 | 1/2013 | Broadbent | |
| 2013/0138578 A1 | 5/2013 | Epstein | |
| 2013/0138758 A1 | 5/2013 | Cohen et al. | |
| 2013/0166346 A1* | 6/2013 | Al-Zuhair | G06Q 10/0635 705/7.28 |
| 2013/0173437 A1 | 7/2013 | Capparell et al. | |
| 2013/0198111 A1 | 8/2013 | DiCastri et al. | |
| 2013/0318004 A1 | 11/2013 | Bass et al. | |
| 2013/0318007 A1 | 11/2013 | Van Harlow et al. | |
| 2013/0325394 A1 | 12/2013 | Yuen et al. | |
| 2013/0325396 A1 | 12/2013 | Yuen et al. | |
| 2013/0325399 A1 | 12/2013 | Yuen et al. | |
| 2013/0325404 A1 | 12/2013 | Yuen et al. | |
| 2013/0339219 A1 | 12/2013 | Bernheimer et al. | |
| 2014/0039840 A1 | 2/2014 | Yuen et al. | |
| 2014/0039842 A1 | 2/2014 | Yuen et al. | |
| 2014/0046871 A1 | 2/2014 | Silverman | |
| 2014/0046872 A1 | 2/2014 | Arnott et al. | |
| 2014/0067714 A1* | 3/2014 | Melton | G06Q 40/06 705/36 R |
| 2014/0067722 A1 | 3/2014 | Milevsky et al. | |
| 2014/0088922 A1 | 3/2014 | Messenger | |
| 2014/0088995 A1 | 3/2014 | Damani | |
| 2014/0108151 A1 | 4/2014 | Bookstaff | |
| 2014/0129402 A1 | 5/2014 | McDonough et al. | |
| 2014/0136381 A1 | 5/2014 | Joseph et al. | |
| 2014/0142967 A1 | 5/2014 | Bedrosian et al. | |
| 2014/0143175 A1 | 5/2014 | Greenshields et al. | |
| 2014/0163430 A1 | 6/2014 | Tropper et al. | |
| 2014/0164287 A1 | 6/2014 | Hyde et al. | |
| 2014/0180962 A1 | 6/2014 | Fiala et al. | |
| 2014/0188758 A1 | 7/2014 | Harper et al. | |
| 2014/0222714 A1 | 8/2014 | Dial et al. | |
| 2014/0249985 A1 | 9/2014 | Scott et al. | |
| 2014/0279382 A1 | 9/2014 | Drakeley et al. | |
| 2014/0279684 A1 | 9/2014 | Liao et al. | |
| 2014/0279701 A1 | 9/2014 | Farrow | |
| 2014/0280219 A1 | 9/2014 | Maser et al. | |
| 2014/0292564 A1 | 10/2014 | Park et al. | |
| 2014/0302470 A1 | 10/2014 | Zapantis et al. | |
| 2014/0337450 A1 | 11/2014 | Choudhary et al. | |
| 2014/0344009 A1* | 11/2014 | Coppinger | G06Q 10/0637 705/7.28 |
| 2014/0365400 A1 | 12/2014 | Fiala et al. | |
| 2014/0372340 A1* | 12/2014 | Brown, III | G06Q 40/06 705/36 R |
| 2014/0372341 A1* | 12/2014 | Brown, III | G06Q 40/06 705/36 R |
| 2015/0095265 A1* | 4/2015 | Feinendegen | G06Q 40/06 705/36 R |
| 2015/0134501 A1 | 5/2015 | Chen et al. | |
| 2015/0134566 A1 | 5/2015 | Chen et al. | |
| 2015/0142622 A1 | 5/2015 | Robertson | |
| 2015/0149217 A1 | 5/2015 | Rath et al. | |
| 2015/0213472 A1 | 7/2015 | Raikula | |
| 2015/0221036 A1* | 8/2015 | Sharma | G06Q 40/06 705/36 R |
| 2015/0262307 A1 | 9/2015 | Krueger | |
| 2015/0262499 A1* | 9/2015 | Wicka | G06Q 50/22 705/14.27 |
| 2016/0063632 A1 | 3/2016 | Folk et al. | |
| 2016/0086277 A1 | 3/2016 | Irlam | |
| 2016/0110813 A1 | 4/2016 | Hayden | |
| 2016/0275608 A1 | 9/2016 | Dintenfass et al. | |
| 2016/0275609 A1 | 9/2016 | Dintenfass et al. | |
| 2016/0275610 A1 | 9/2016 | Dintenfass et al. | |
| 2016/0275611 A1 | 9/2016 | Dintenfass et al. | |
| 2016/0275612 A1 | 9/2016 | Wadley et al. | |
| 2016/0275613 A1 | 9/2016 | Dintenfass et al. | |
| 2016/0275615 A1 | 9/2016 | Dintenfass et al. | |
| 2016/0275616 A1 | 9/2016 | Nicholson et al. | |
| 2016/0321935 A1 | 11/2016 | Mohler et al. | |
| 2016/0358258 A1 | 12/2016 | Dintenfass et al. | |
| 2016/0364801 A1 | 12/2016 | Dintenfass et al. | |

OTHER PUBLICATIONS

AHA selects holman automotive as worksite fitness innovation company of 2011. (2012). Entertainment Close-Up, , NA. Retrieved from https://dialog.proquest.com/professional/docview/914778406?accountid=142257 retrieved on Mar. 2, 2018 (Year: 2011).*

Omron healthcare offers holiday gifts for health enthusiasts. (2010). Wireless News, , NA. Retrieved from https://dialog.proquest.com/professional/docview/820400191?accountid=142257 retrieved on Mar. 2, 2018 (Year: 2010).*

Extended European Search Report dated Jan. 29, 2010 for European Patent Application EP 09 25 2414.9; 11 pages.

Minna Pura, Linking Perceived Value and Loyalty in Location-Based Mobile Services Managing Service Quality, (2005) 509-538 vol. 15.6.

The Fidelity Income Management Account http://personal.fidelity.com/planning/retirement/retiree/content/m=imaderno.shtml#, screenshot taken on Jun. 25, 2015, from Internet Archive WaybackMachine, 1 page.

International Search Report for PCTUS201035192 dated Jun. 27, 2010 3 pages.

"How Long Will My Money Last With Systematic Withdrawals?"; Mutual of Omaha, Calculators, retrieved on May 7, 2015 from

(56) References Cited

OTHER PUBLICATIONS http://www.mutualofomaha.com/tools/calculators/retirement-planning/how-long-my-money-last.php; 1 page.

* cited by examiner

```
                    ┌─────────────────────────────────────────┐
                    │     RETRIEVE CREATED RETIREMENT SCORE    │
                    │                  503                     │
                    └─────────────────────────────────────────┘
                                       │
                                       ▼
                    ┌─────────────────────────────────────────┐
                    │  RETRIEVE DETERMINED RECOMMENDATIONS FOR │
                    │      RETIREMENT SCORE IMPROVEMENT        │
                    │                  505                     │
                    └─────────────────────────────────────────┘
                                       │
                                       ▼
                    ┌─────────────────────────────────────────┐
                    │ RETRIEVE HISTORIC RETIREMENT SCORE DATA FOR USER │
                    │                  507                     │
                    └─────────────────────────────────────────┘
                                       │
                                       ▼
                    ┌─────────────────────────────────────────┐
                    │  PRESENT HISTORIC RETIREMENT SCORE DATA TO USER VIA │
                    │                INTERFACE                 │
                    │                  509                     │
                    └─────────────────────────────────────────┘
                                       │
                                       ▼
                    ┌─────────────────────────────────────────┐
                    │    AUGMENT HISTORIC RETIREMENT SCORE DATA WITH    │
                    │ RECOMMENDATIONS AT VARIOUS HISTORIC TIME POINTS   │
                    │                  511                     │
                    └─────────────────────────────────────────┘
                                       │
                                       ▼
                    ┌─────────────────────────────────────────┐
                    │ ILLUSTRATE RECOMMENDATIONS EFFECT ON CURRENT │
                    │ RETIREMENT SCORE IF IMPLEMENTED HISTORICALLY │
                    │                  513                     │
                    └─────────────────────────────────────────┘
```

FIGURE 5B

SYSTEM FOR ACCOUNT LINKING AND FUTURE EVENT INTEGRATION INTO RETIREMENT SCORE CALCULATION

FIELD

In general, embodiments of the invention relate to retirement planning, in particular, embodiments of the invention relate to a framework for assessment of retirement planning by providing a retirement score for at least a first user and a second user based on the first and second user linking user profiles of the first user and the second user.

BACKGROUND

Retirement planning, in a financial context, refers to the allocation of savings or revenue for retirement in an attempt to achieve financial independence, so that the need to be gainfully employed is optional rather than a necessity. Most retirement planning models provide a target sum that the user should save before retirement, but fail to determine a projected retirement score based on multiple users linking profiles together.

SUMMARY

Embodiments of the present invention address the above needs and/or achieve other advantages by providing apparatuses (e.g., a system, computer program product, and/or other device) and methods for a system to allow a user to join a retirement group based on determining a projected retirement score for the user.

In one embodiment, a system for assessing retirement planning based on a projected retirement score is presented a memory, a communication device connected to a distributed network, a processing device operatively coupled to the memory and the communication device, a software module stored in memory comprising executable instructions that when executed by the processing device, cause the processing device to: compile into a structured database connected to the distributed network projected retirement information of a first user, wherein the retirement information comprises a user profile of the first user; generate a projected retirement score based on the projected retirement information of the first use, wherein the projected retirement score is an estimate of the user's preparedness for retirement at a future predetermined date; receive from a personal computing device connected to the distributed network, a request to link a user profile for a second user to the user profile of the first user; authorize the request to link the user profile of the second user with the user profile of the first user based at least in part on an association between the first user and the second user; compile into the structured database projected retirement information of the second user based on authorizing the request to link the user profile of the second user to the user profile of the first user; combine the projected retirement information of the first user with the projected retirement information of the second user, thus resulting in combined projected retirement information; update the projected retirement score based on the combined projected retirement information; and communicate to the personal computing device, via the communication device, the projected retirement score.

In some embodiments, the retirement information comprises at least financial account information, retirement account information.

In one embodiment, a system for assessing retirement planning based on a projected retirement score is presented a memory, a communication device connected to a distributed network, a processing device operatively coupled to the memory and the communication device, a software module stored in memory comprising executable instructions that when executed by the processing device, cause the processing device to: determine an expected age of retirement of at least the first user and the second user; determine a number of years before the first user retires based on the expected age of retirement of the first user; determine a number of years before the second user retires based on the expected age of retirement of the second user; wherein, generating the projected retirement score is further based on the number of years before the first user retires; and wherein, updating the projected retirement score is further based on the number of years before the second user retires.

In one embodiment, a system for assessing retirement planning based on a projected retirement score is presented a memory, a communication device connected to a distributed network, a processing device operatively coupled to the memory and the communication device, a software module stored in memory comprising executable instructions that when executed by the processing device, cause the processing device to receive payment information for future payments of the first user or the second user, wherein, generating the projected retirement score is further based on the future payments of the first user, and wherein, updating the projected retirement score is further based on the future payments of the second user.

In one embodiment, a system for assessing retirement planning based on a projected retirement score is presented a memory, a communication device connected to a distributed network, a processing device operatively coupled to the memory and the communication device, a software module stored in memory comprising executable instructions that when executed by the processing device, cause the processing device to determine a difference between the generated projected retirement score and the updated projected retirement score, and communicate to the personal computing device, via the communication device, the difference between the generated projected retirement score and the updated projected retirement score.

In one embodiment, a system for assessing retirement planning based on a projected retirement score is presented a memory, a communication device connected to a distributed network, a processing device operatively coupled to the memory and the communication device, a software module stored in memory comprising executable instructions that when executed by the processing device, cause the processing device to determine an expected increase in earnings of the first user and the second user, wherein generating the projected retirement score is further based on the expected increase in earning of the first user, and wherein, updating the projected retirement score is further based on the expected increase in earning of the second user.

In some embodiments, the expected increase in earnings comprises expected funds from retirement programs.

BRIEF DESCRIPTION OF THE DRAWINGS

Figure 1:
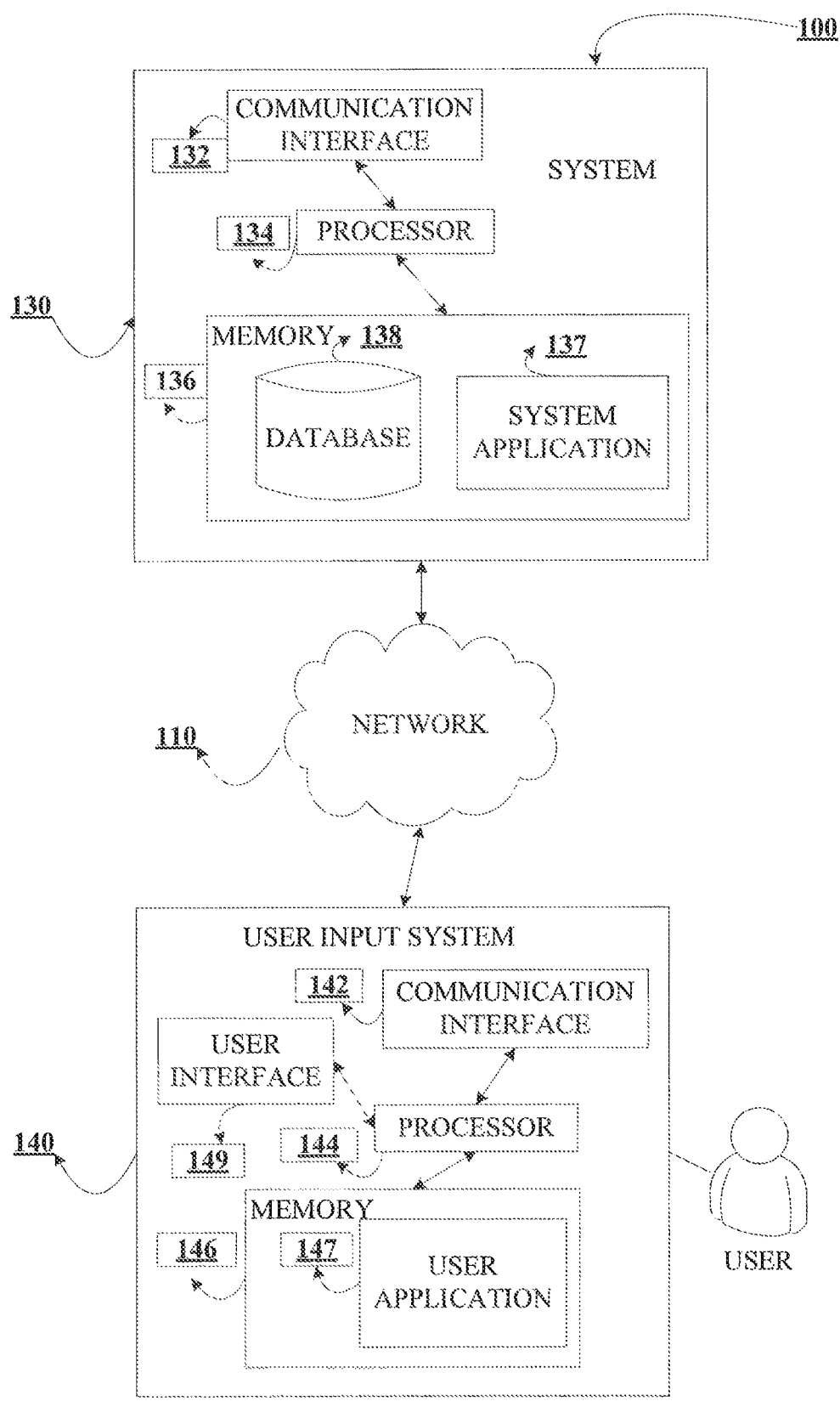
Figure 2:
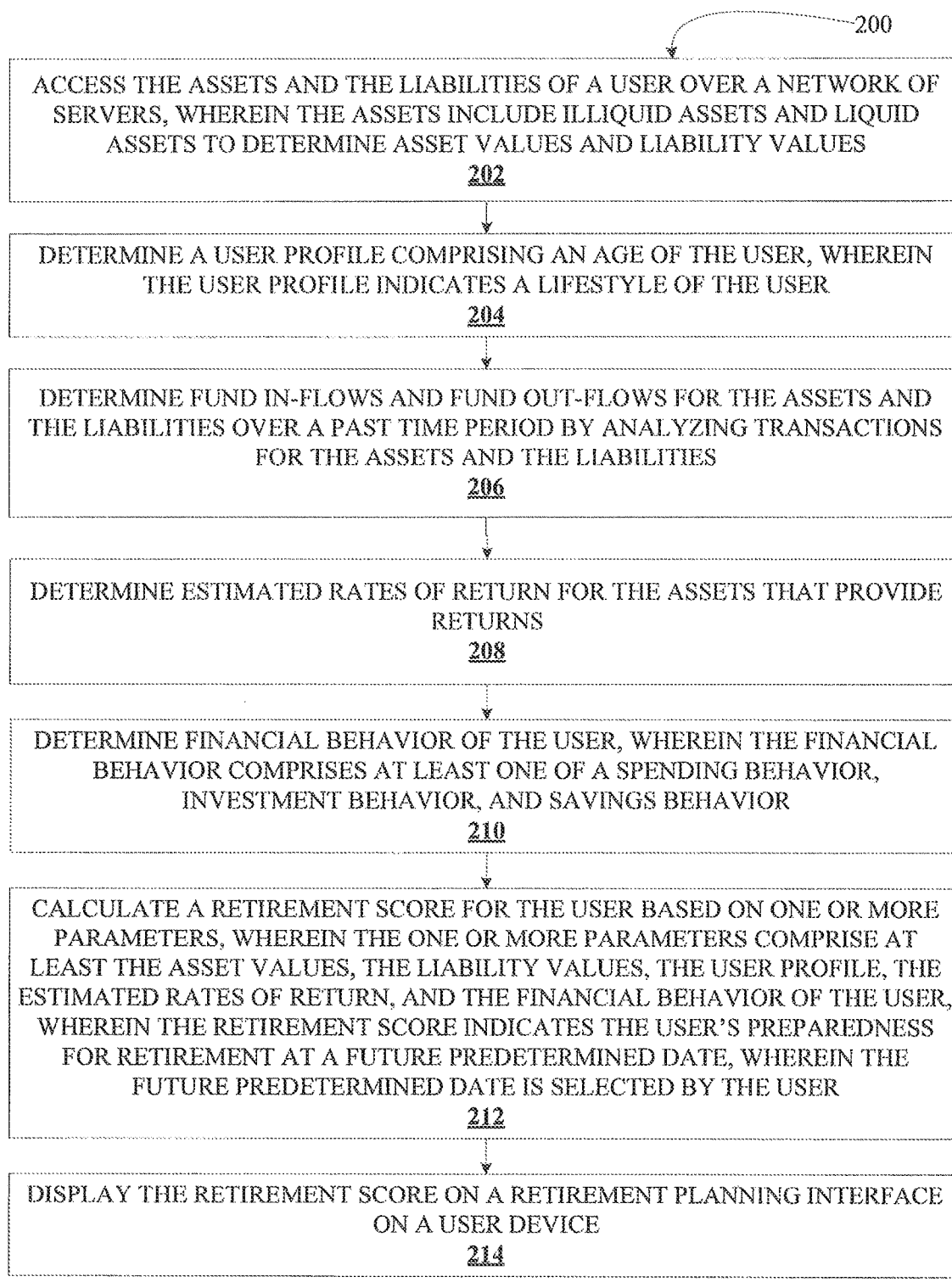
Figure 3:
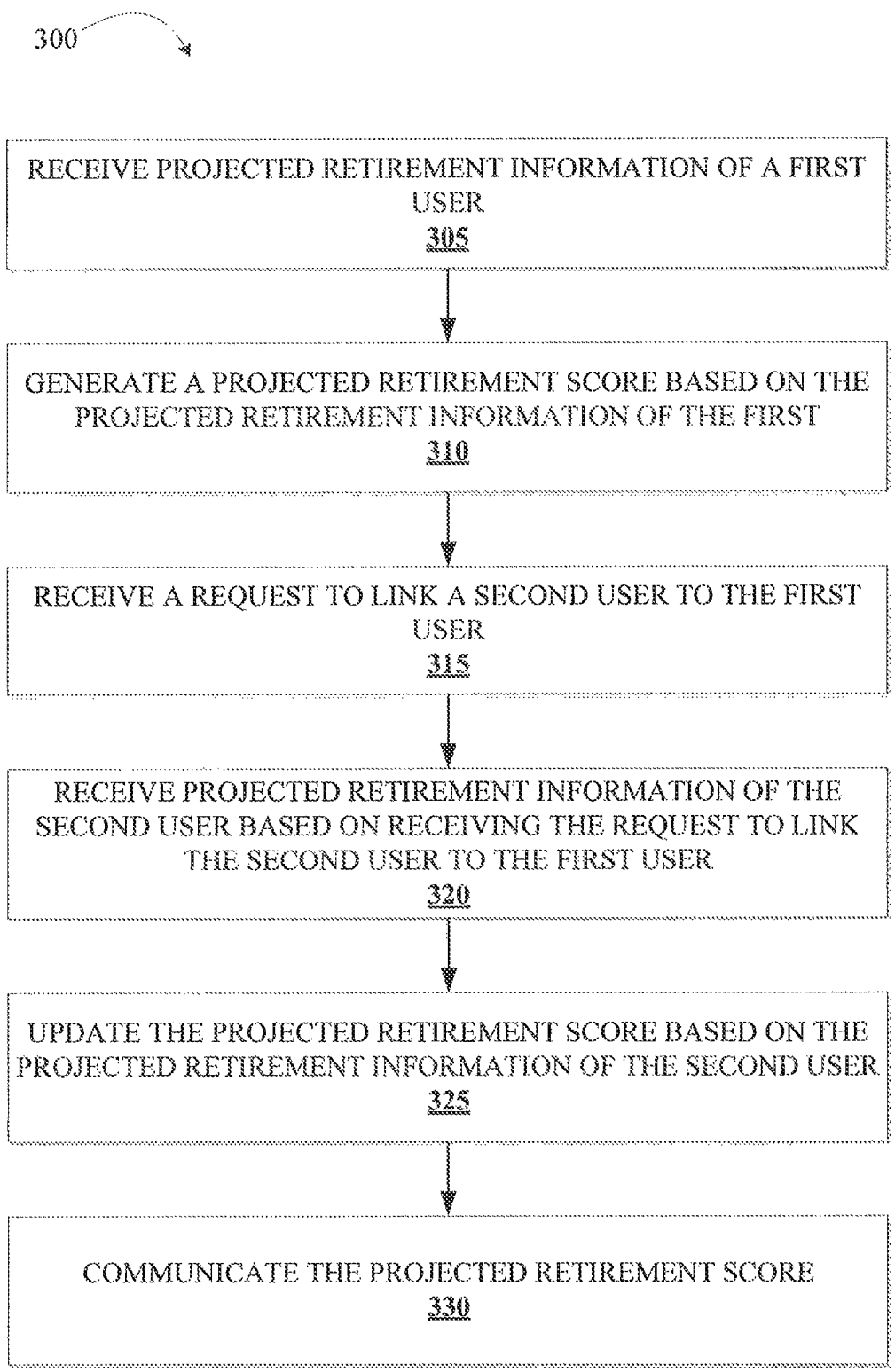
Figure 4A:
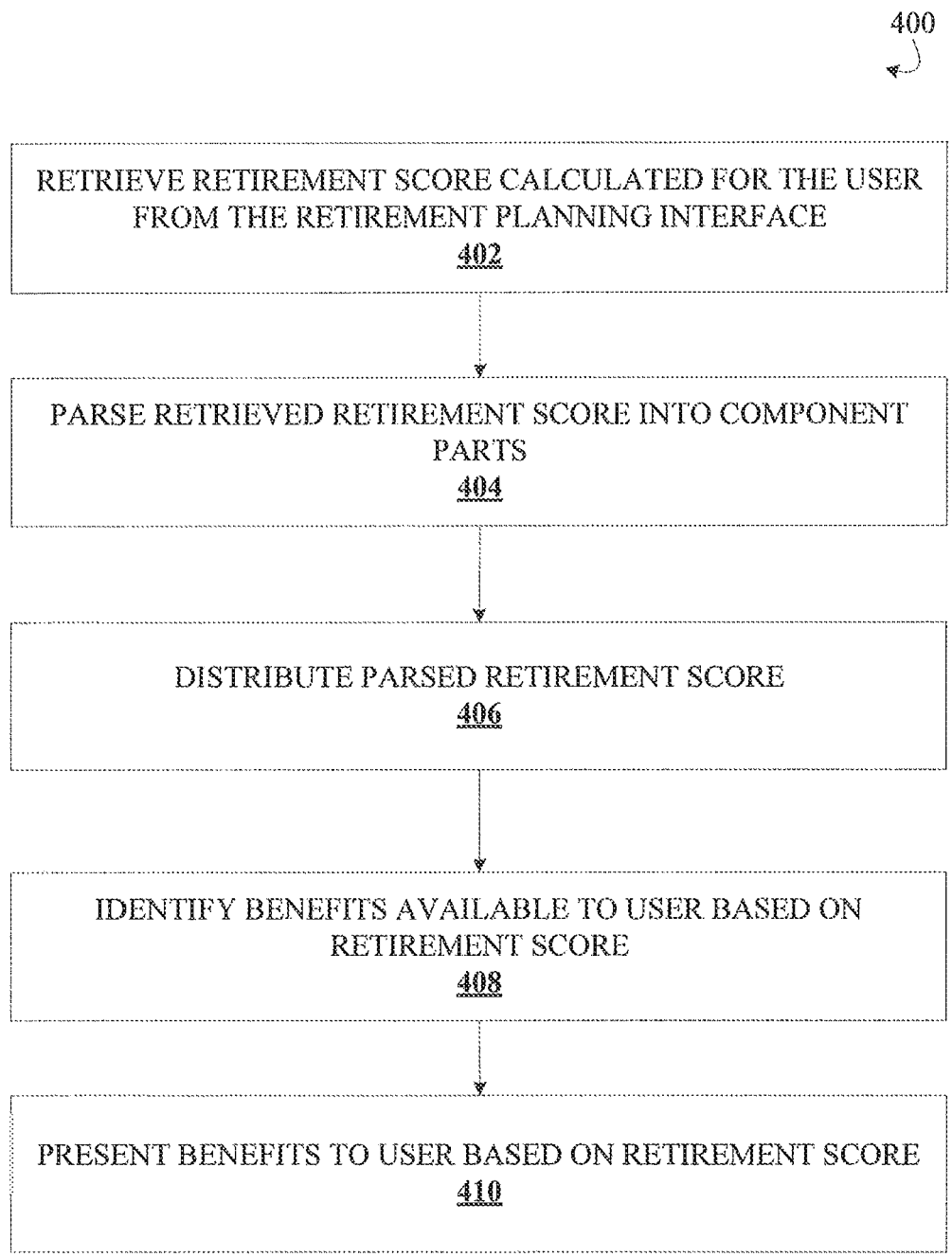
Figure 4B:
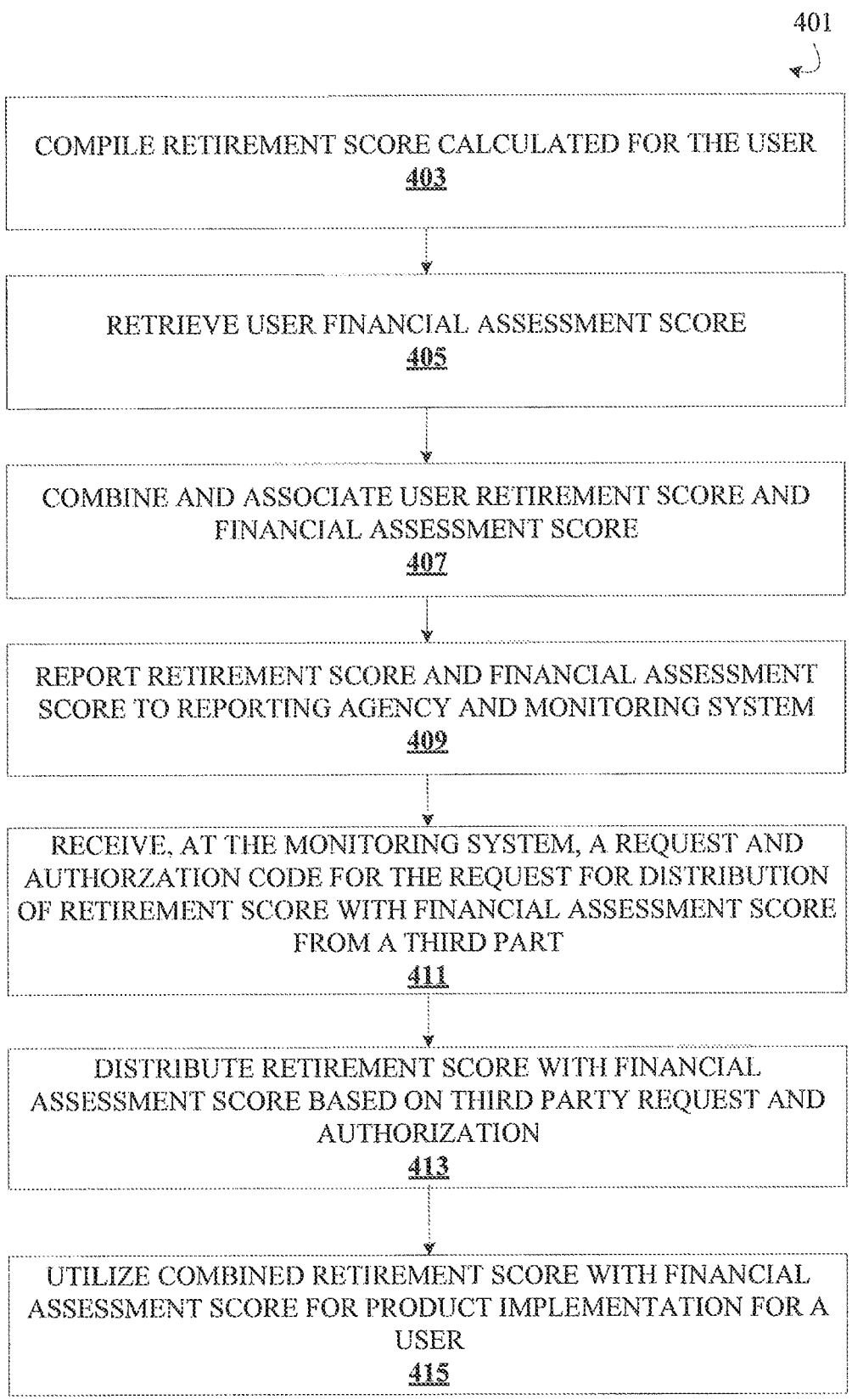
Figure 5A:
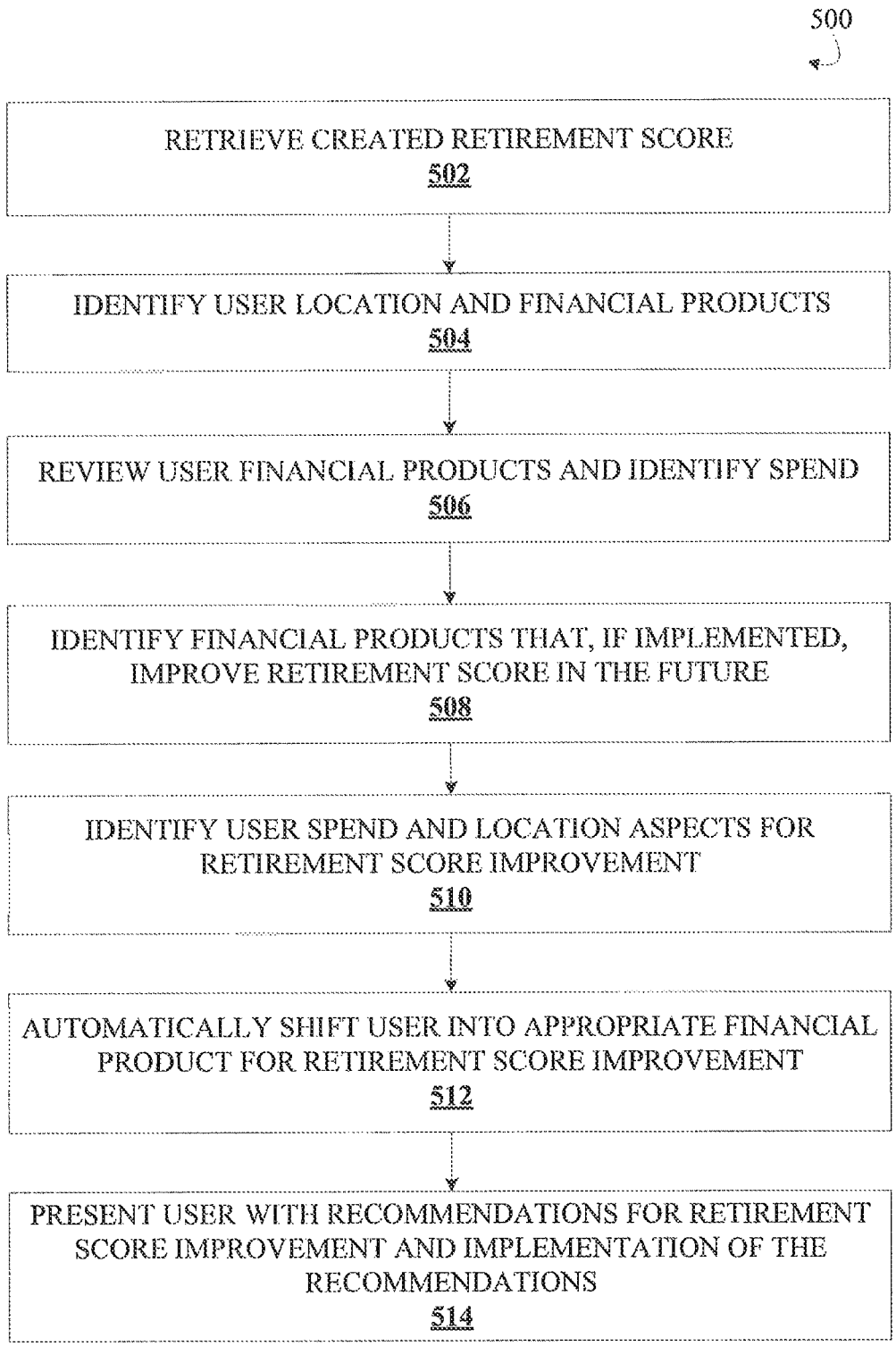
Figure 6:
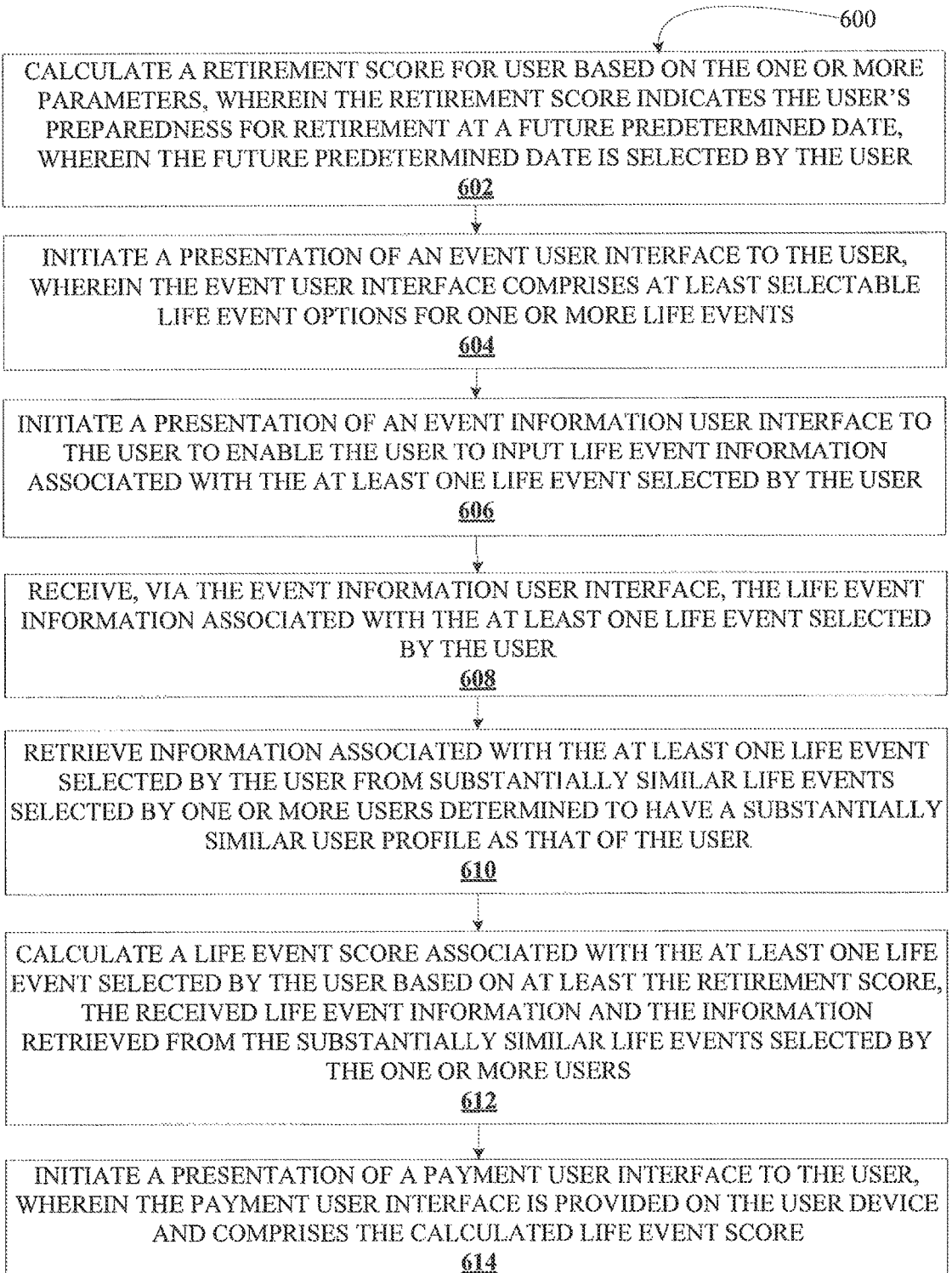
Figure 7A:
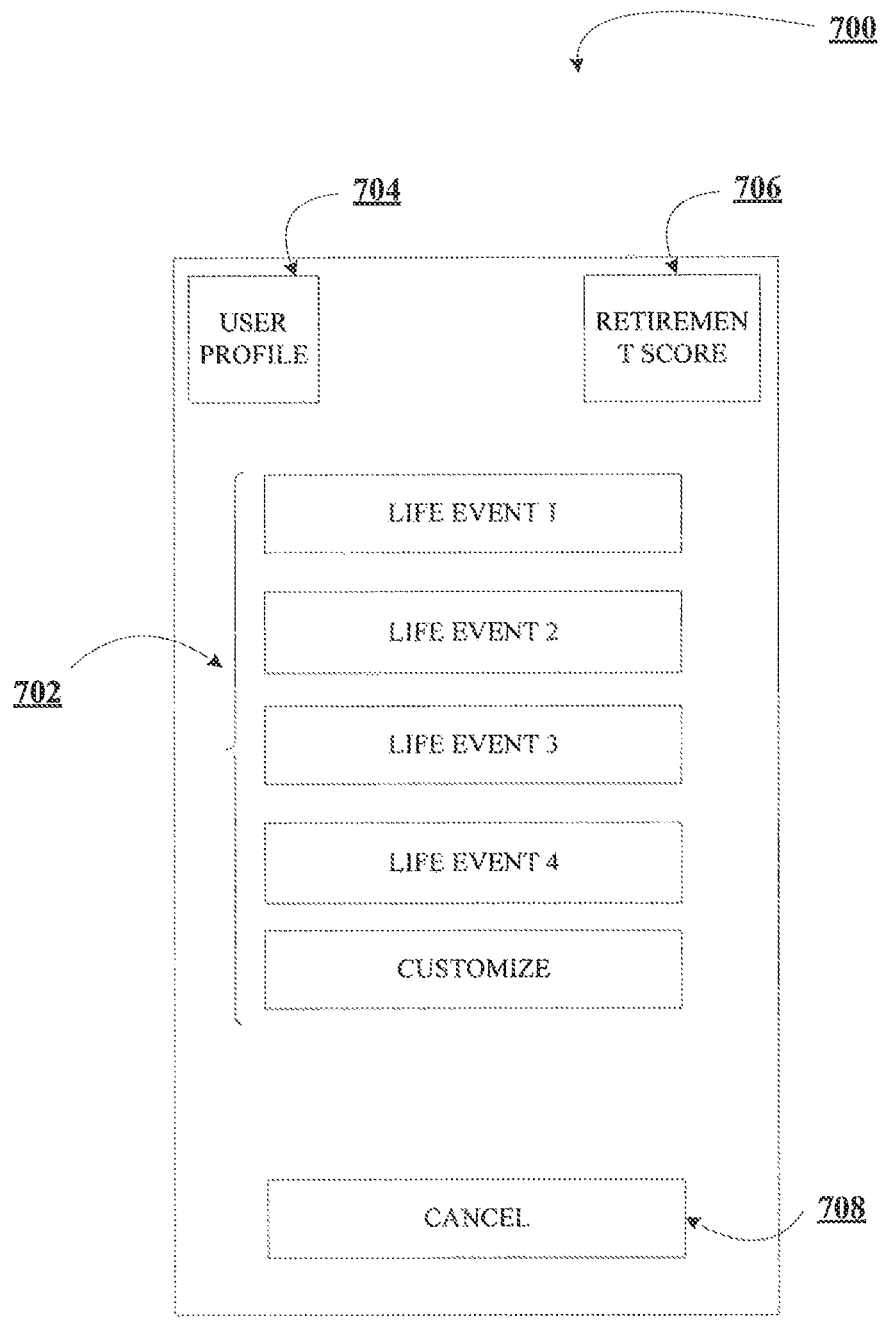
Figure 7B:
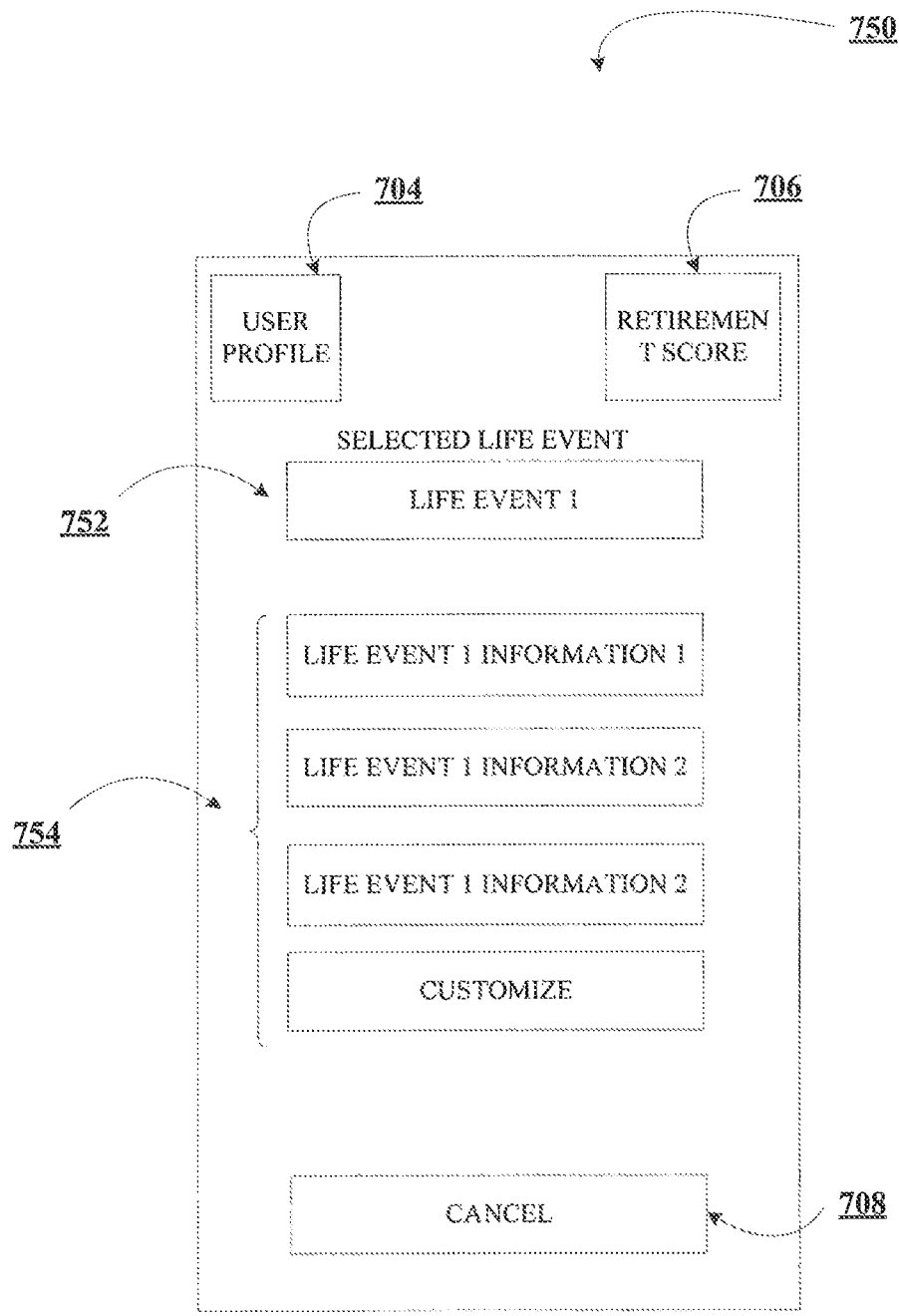
Figure 8:
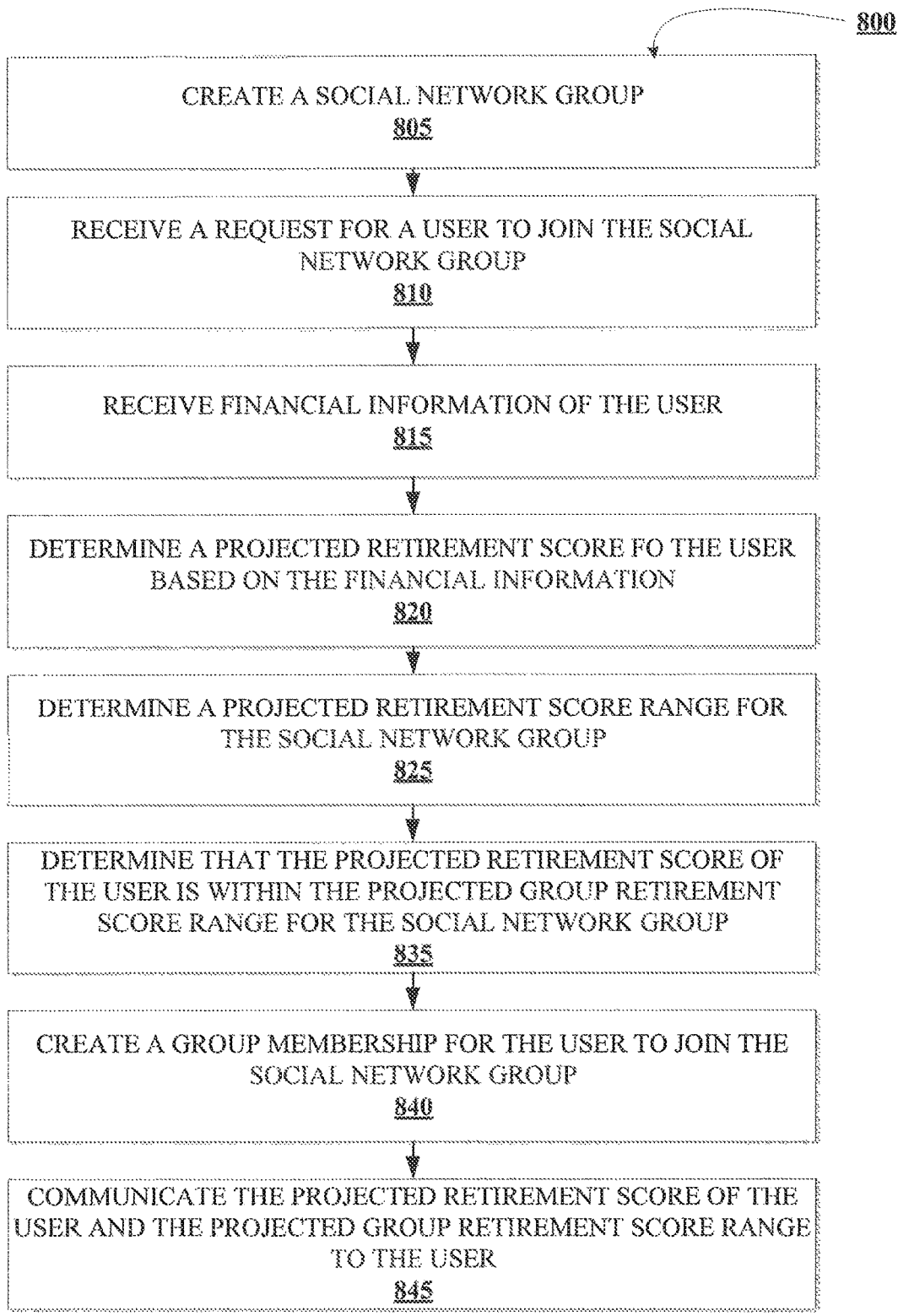
Figure 9:
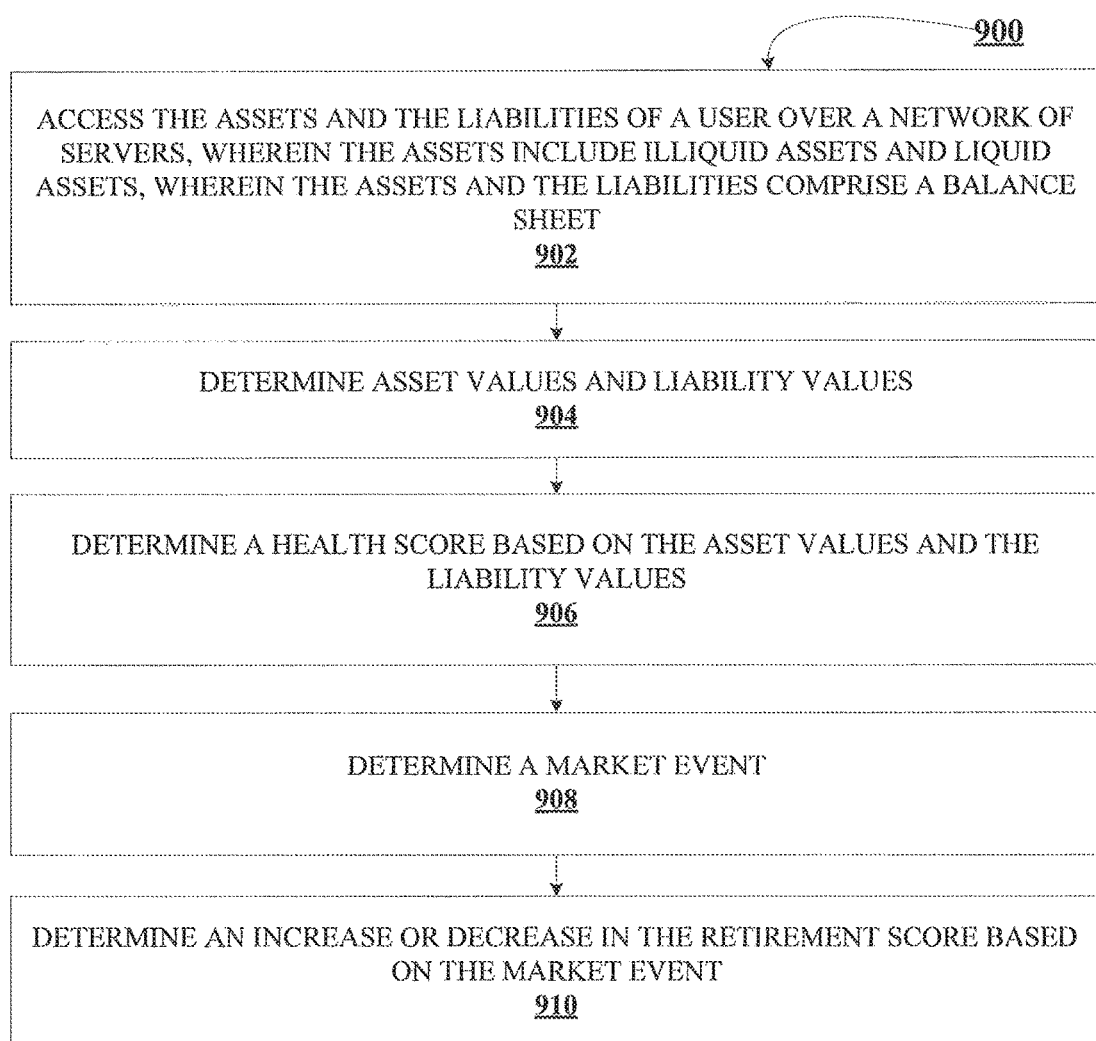
Figure 10:
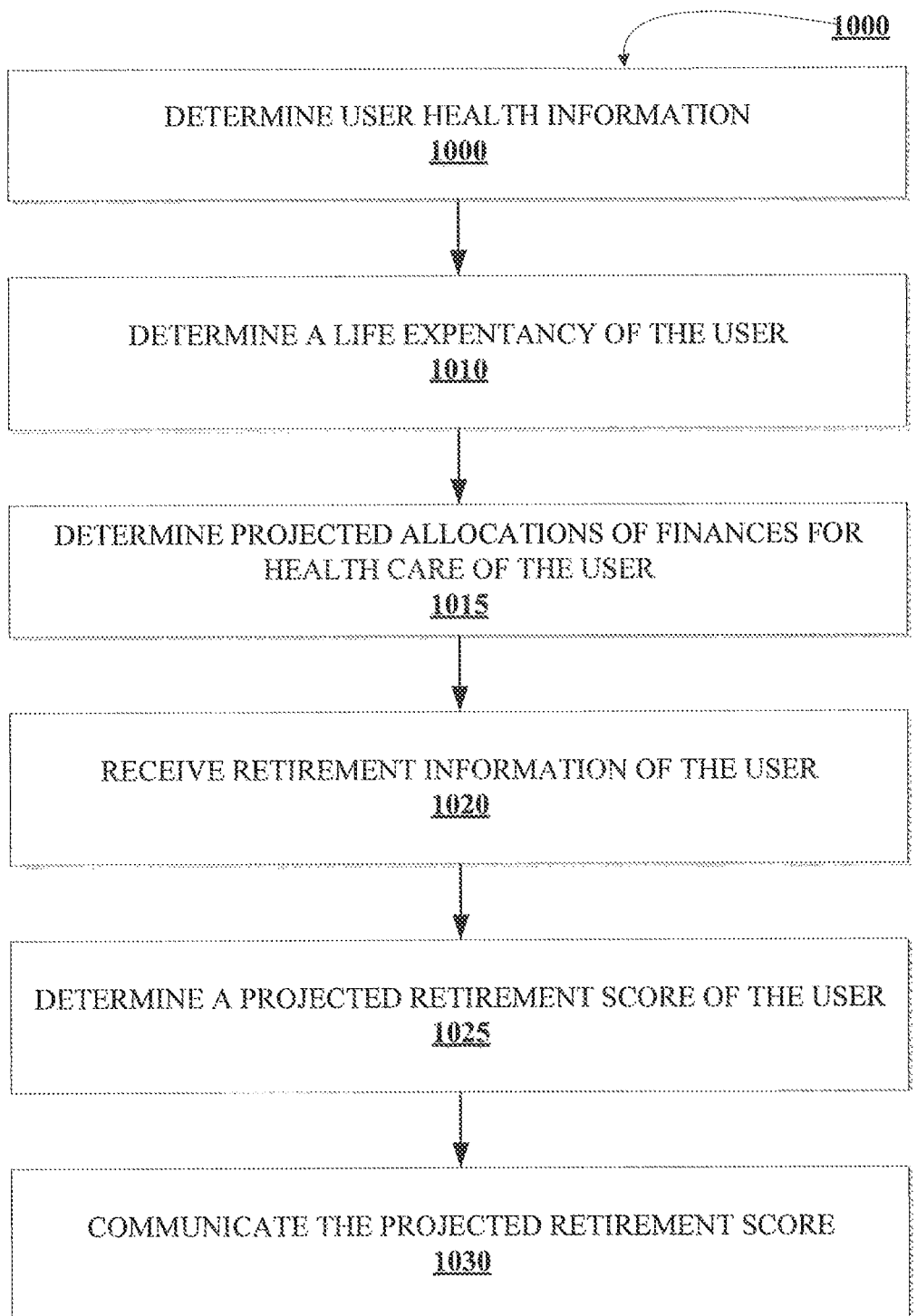
Figure 11:
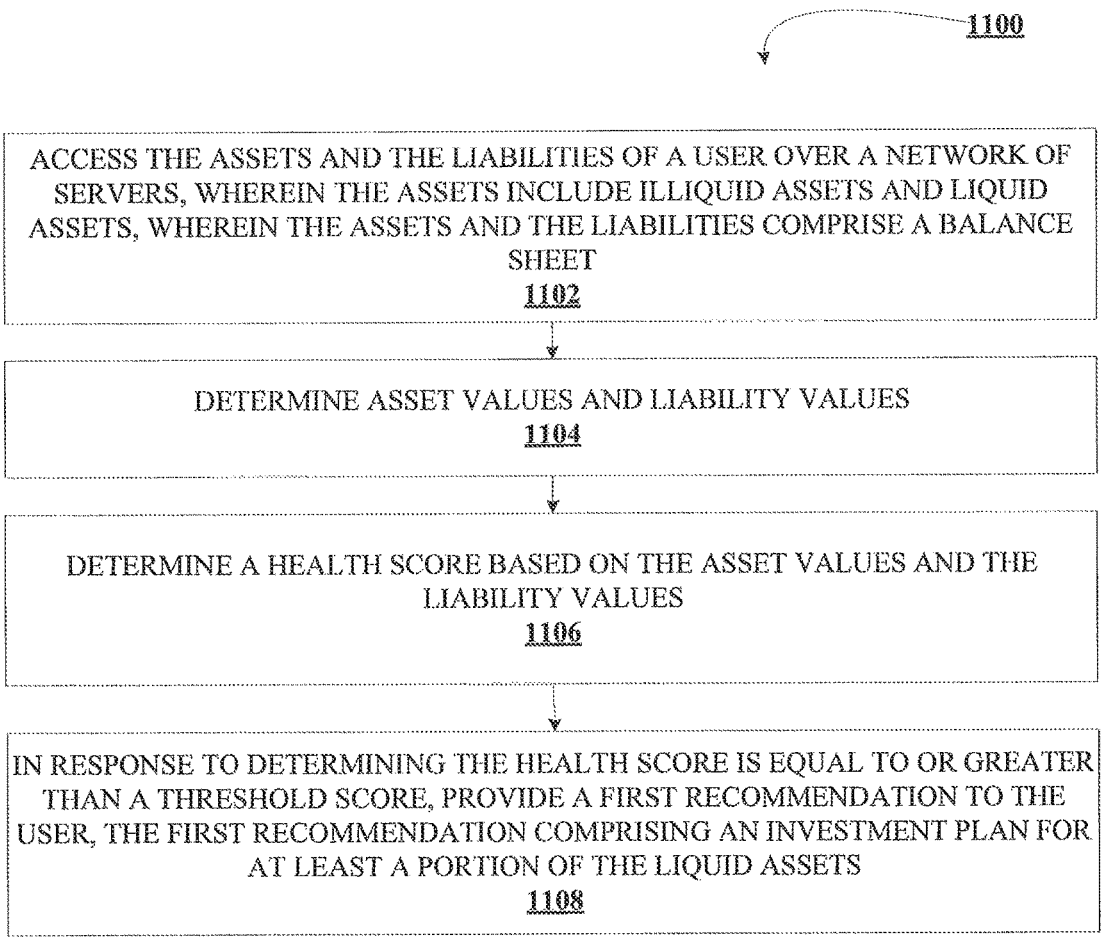

Having thus described embodiments of the invention in general terms, reference will be made to the accompanying drawings, where:

FIG. 1 presents an exemplary block diagram of the system environment 100 for implementing the process flows described herein in accordance with embodiments of the present invention;

FIG. 2 illustrates a high level process flow for assessing retirement planning based on a retirement score in accordance with embodiments of the present invention;

FIG. 3 illustrates a high level process flow for determining a projected retirement score based on linking user profiles in accordance with embodiments of the present invention;

FIG. 4A illustrates utilizing the determined retirement score for benefit qualification determination, in accordance with some embodiments of the invention;

FIG. 4B illustrates a process flow for reporting and utilizing the retirement score for third party presentment, in accordance with some embodiments of the invention;

FIG. 5A illustrates a high level process flow for optimization of a user retirement score in accordance with embodiments of the present invention;

FIG. 5B illustrates a process flow for reverse review of retirement score calculations based on recommendations in accordance with embodiments of the present invention;

FIG. 6 illustrates a high level process flow for assessing impact of life events on retirement planning in accordance with embodiments of the present invention;

FIG. 7A illustrates an exemplary retirement planning user interface 700 in accordance with embodiments of the invention;

FIG. 7B illustrates an exemplary event information user interface 750 in accordance with embodiments of the invention;

FIG. 8 illustrates a high level process flow for creating a social network group membership for a user based on a projected retirement score of the user in accordance with embodiments of the present invention;

FIG. 9 illustrates a high level process flow for assessing retirement planning based on a retirement score and a market event in accordance with embodiments of the present invention;

FIG. 10 illustrates a high level process flow for determining a projected retirement score in accordance with embodiments of the present invention; and FIG. 11 illustrates a high level process flow for assessing retirement planning based on a retirement score and investments associated with the user in accordance with embodiments of the present invention.

DETAILED DESCRIPTION OF THE INVENTION

Embodiments of the present invention now may be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

In some embodiments, a "user" may be a financial institution customer (e.g., an account holder or a person who have an account (e.g., banking account, credit account, or the like)). In one aspect, a user may be any financial institution customer involved in retirement planning with the financial institution or any other affiliate entities associated with the financial institution. In some embodiments, the user may be an individual who may be interested in opening an account with the financial institution. In some other embodiments, a user may be any individual who may be interested in enrolling in the retirement plan offered by the financial institution. In some embodiments, a "user" may be a financial institution employee (e.g., an underwriter, a project manager, an IT specialist, a manager, an administrator, an internal operations analyst, bank teller or the like) capable of operating the system described herein. For purposes of this invention, the term "user" and "customer" may be used interchangeably.

In some embodiments, an "entity" as used herein may be a financial institution. For the purposes of this invention, a "financial institution" may be defined as any organization, entity, or the like in the business of moving, investing, or lending money, dealing in financial instruments, or providing financial services. This may include commercial banks, thrifts, federal and state savings banks, savings and loan associations, credit unions, investment companies, insurance companies and the like. In some embodiments, the entity may allow a user to establish an account with the entity. An "account" may be the relationship that the user has with the entity. Examples of accounts include a deposit account, such as a transactional account (e.g. a banking account), a savings account, an investment account, a money market account, a time deposit, a demand deposit, a pre-paid account, a credit account, a non-monetary user profile that includes only personal information associated with the user, or the like. The account is associated with and/or maintained by an entity. In other embodiments, an "entity" may not be a financial institution.

As used herein, a "user interface" may be a graphical user interface. Typically, a graphical user interface (GUI) is a type of interface that allows users to interact with electronic devices such as graphical icons and visual indicators such as secondary notation, as opposed to using only text via the command line. In some embodiments, the graphical user interface may include both graphical elements and text elements.

FIG. 1 presents an exemplary block diagram of the system environment 100 for implementing the process flows described herein in accordance with embodiments of the present invention. As illustrated, the system environment 100 includes a network 110, a system 130, and a user input system 140. Also shown in FIG. 1 is a user of the user input system 140. The user input system 140 may be a mobile device or other non-mobile computing device. The user may be a person who uses the user input system 140 to execute a user application 147. The user application 147 may be an application to communicate with the system 130, perform a transaction, input information onto a user interface presented on the user input system 140, or the like. The user application 147 and/or the system application 137 may incorporate one or more parts of any process flow described herein.

As shown in FIG. 1, the system 130, and the user input system 140 are each operatively and selectively connected to the network 110, which may include one or more separate networks. In addition, the network 110 may include a telecommunication network, local area network (LAN), a wide area network (WAN), and/or a global area network (GAN), such as the Internet. It will also be understood that the network 110 may be secure and/or unsecure and may also include wireless and/or wired and/or optical interconnection technology.

The user input system 140 may include any computerized apparatus that can be configured to perform any one or more of the functions of the user input system 140 described and/or contemplated herein. For example, the user may use the user input system 140 to transmit and/or receive information or commands to and from the system 130. In some embodiments, for example, the user input system 140 may include a personal computer system (e.g. a non-mobile or non-portable computing system, or the like), a mobile computing device, a personal digital assistant, a mobile phone, a tablet computing device, a network device, and/or the like. As illustrated in FIG. 1, in accordance with some embodiments of the present invention, the user input system 140 includes a communication interface 142, a processor 144, a memory 146 having an user application 147 stored therein, and a user interface 149. In such embodiments, the communication interface 142 is operatively and selectively connected to the processor 144, which is operatively and selectively connected to the user interface 149 and the memory 146. In some embodiments, the user may use the user application 147 to execute processes described with respect to the process flows described herein. Specifically, the user application 147 executes the process flows described herein.

Each communication interface described herein, including the communication interface 142, generally includes hardware, and, in some instances, software, that enables the user input system 140, to transport, send, receive, and/or otherwise communicate information to and/or from the communication interface of one or more other systems on the network 110. For example, the communication interface 142 of the user input system 140 may include a wireless transceiver, modem, server, electrical connection, and/or other electronic device that operatively connects the user input system 140 to another system such as the system 130. The wireless transceiver may include a radio circuit to enable wireless transmission and reception of information. Additionally, the user input system 140 may include a positioning system. The positioning system (e.g. a global positioning system (GPS), a network address (IP address) positioning system, a positioning system based on the nearest cell tower location, or the like) may enable at least the user input system 140 or an external server or computing device in communication with the user input system 140 to determine the location (e.g. location coordinates) of the user input system 140.

Each processor described herein, including the processor 144, generally includes circuitry for implementing the audio, visual, and/or logic functions of the user input system 140. For example, the processor may include a digital signal processor device, a microprocessor device, and various analog-to-digital converters, digital-to-analog converters, and other support circuits. Control and signal processing functions of the system in which the processor resides may be allocated between these devices according to their respective capabilities. The processor may also include functionality to operate one or more software programs based at least partially on computer-executable program code portions thereof, which may be stored, for example, in a memory device, such as in the user application 147 of the memory 146 of the user input system 140.

Each memory device described herein, including the memory 146 for storing the user application 147 and other information, may include any computer-readable medium. For example, memory may include volatile memory, such as volatile random access memory (RAM) having a cache area for the temporary storage of information. Memory may also include non-volatile memory, which may be embedded and/or may be removable. The non-volatile memory may additionally or alternatively include an EEPROM, flash memory, and/or the like. The memory may store any one or more of pieces of information and data used by the system in which it resides to implement the functions of that system.

As shown in FIG. 1, the memory 146 includes the user application 147. In some embodiments, the user application 147 includes an interface for communicating with, navigating, controlling, configuring, and/or using the user input system 140. In some embodiments, the user application 147 includes computer-executable program code portions for instructing the processor 144 to perform one or more of the functions of the user application 147 described and/or contemplated herein. In some embodiments, the user application 147 may include and/or use one or more network and/or system communication protocols.

Also shown in FIG. 1 is the user interface 149. In some embodiments, the user interface 149 includes one or more output devices, such as a display and/or speaker, for presenting information to the user. In some embodiments, the user interface 149 includes one or more input devices, such as one or more buttons, keys, dials, levers, directional pads, joysticks, accelerometers, controllers, microphones, touchpads, touchscreens, haptic interfaces, microphones, scanners, motion detectors, cameras, and/or the like for receiving information from the user. In some embodiments, the user interface 149 includes the input and display devices of a mobile device, which are operable to receive and display information.

FIG. 1 also illustrates a system 130, in accordance with an embodiment of the present invention. The system 130 may refer to the "apparatus" described herein. The system 130 may include any computerized apparatus that can be configured to perform any one or more of the functions of the system 130 described and/or contemplated herein. In accordance with some embodiments, for example, the system 130 may include a computer network, an engine, a platform, a server, a database system, a front end system, a back end system, a personal computer system, and/or the like. Therefore, the system 130 may be a server managed by the business. The system 130 may be located at the facility associated with the business or remotely from the facility associated with the business. In some embodiments, such as the one illustrated in FIG. 1, the system 130 includes a communication interface 132, a processor 134, and a memory 136, which includes a system application 137 and a structured database 138 stored therein. As shown, the communication interface 132 is operatively and selectively connected to the processor 134, which is operatively and selectively connected to the memory 136.

It will be understood that the system application 137 may be configured to implement any one or more portions of the various user interfaces and/or process flow described herein. The system application 137 may interact with the user application 147. It will also be understood that, in some embodiments, the memory includes other applications. It will also be understood that, in some embodiments, the system application 137 is configured to communicate with the structured database 138, the user input system 140, or the like.

It will be further understood that, in some embodiments, the system application 137 includes computer-executable program code portions for instructing the processor 134 to perform any one or more of the functions of the system application 137 described and/or contemplated herein. In some embodiments, the system application 137 may include and/or use one or more network and/or system communication protocols.

In addition to the system application 137, the memory 136 also includes the structured database 138. As used herein, the structured database 138 may be one or more distinct and/or remote databases. In some embodiments, the structured database 138 is not located within the system and is instead located remotely from the system. In some embodiments, the structured database 138 stores information or data described herein.

It will be understood that the structured database 138 may include any one or more storage devices, including, but not limited to, datastores, databases, and/or any of the other storage devices typically associated with a computer system. It will also be understood that the structured database 138 may store information in any known way, such as, for example, by using one or more computer codes and/or languages, alphanumeric character strings, data sets, figures, tables, charts, links, documents, and/or the like. Further, in some embodiments, the structured database 138 may include information associated with one or more applications, such as, for example, the system application 137. It will also be understood that, in some embodiments, the structured database 138 provides a substantially real-time representation of the information stored therein, so that, for example, when the processor 134 accesses the structured database 138, the information stored therein is current or substantially current.

It will be understood that the embodiment of the system environment illustrated in FIG. 1 is exemplary and that other embodiments may vary. As another example, in some embodiments, the system 130 includes more, less, or different components. As another example, in some embodiments, some or all of the portions of the system environment 100 may be combined into a single portion. Likewise, in some embodiments, some or all of the portions of the system 130 may be separated into two or more distinct portions.

In addition, the various portions of the system environment 100 may be maintained for and/or by the same or separate parties. It will also be understood that the system 130 may include and/or implement any embodiment of the present invention described and/or contemplated herein. For example, in some embodiments, the system 130 is configured to implement any one or more of the embodiments of the process flows described and/or contemplated herein in connection any process flow described herein. Additionally, the system 130 or the user input system 140 is configured to initiate presentation of any of the user interfaces described herein.

FIG. 2 illustrates a high level process flow for assessing retirement planning based on a retirement score 200. As illustrated by block 202, embodiments of the invention comprise receiving accessing the assets and liabilities of a user over a network of distributed servers, wherein the assets include illiquid assets and liquid assets. The user's assets may include but are not limited to checking accounts, savings accounts, investment accounts (e.g., with regular disbursements and penalties for principal withdrawals, or self-directed accounts that more liquid without penalties), annuity accounts (e.g., social security, claim awards, reverse mortgages, or the like), insurances benefit accounts (e.g., one time or reoccurring), property owned by the user (e.g., investment property, rental property, or the like), or other like assets that may provide regular or semi-regular recurring payments, assets that are or are similar to cash accounts, or assets that need to be sold in order to realize cash values of the assets. In some embodiments the assets may be illiquid (e.g., have penalties or may take time to convert into cash) or may be liquid (e.g., can be converted to cash in a couple of days without penalty). In one aspect, the process flow includes determining a user's asset values (e.g., balances of the account, current or estimated future fair market values of the property, or the like) and liability values (e.g., amount owed, or the like). The user's liabilities may include a mortgage, long and short term debit, payments owed on other personal property or legal judgments against the user, or the like). In some embodiments all of the assets and liabilities are determined in order to get an idea of what the values of the assets and liabilities are in order to determine how long the inflows and outflows for the user may last.

As shown in block 204, embodiments of the invention further include determining a user profile comprising an age of the user, wherein the user profile indicates a lifestyle of the user. In this regard, the system may be configured to determine the user profile based on at least one or more past transactions of the user, a geographic location of the user, an income level, an amount of outgoing funds, asset values, liability values, asset types, spending habits, saving habits or the like. In one aspect, the user profile includes at least information identifying the user. In some embodiments, the system may be configured to establish predefined user profiles including, but not limited to travel profiles, homebody, luxury spender, thrifty saver, risk taker, or the like. For example, for the thrifty saver lifestyle the user may indicate that he/she may downsize the user's home in retirement, sell a vacation home, reduce travel expenses, or the like. The profiles may be pre-programmed by the financial institution and/or programmable by the user to illustrate how the user plans on living in retirement. Other lifestyles illustrate if the user will spend less, the same, or more during retirement.

In some embodiments, the system may be configured to enable the user to customize the user profile. In this regard, the system may be configured to enable the user to select at least one of the predetermined user profiles and customize the at least one selected user profile according to the characteristics of the user by providing additional information. In one aspect, the system may be configured to initiate presentation of one or more selectable options on the retirement planning interface on the user device to enable the user to provide the additional information to customize the selected predetermined user profile.

As shown in block 206, embodiments of the invention further include determining fund in-flows and fund outflows for the assets and liabilities over a past time period by analyzing transactions for the assets and the liabilities. In one aspect, the fund in-flows include funds received from or deposited into the user's assets (e.g., user's accounts, or the like), such as paychecks, 401K disbursements, pension disbursements, or the like. Block 206 further illustrates that past outflows of funds from the user's assets (e.g., user's accounts, or the like) are determined, such as payments for housing (e.g., rent or mortgage), bills, health care insurance and other costs, heat, water, food, or like, which illustrates all of the essential (e.g., necessary or necessary to the user) costs that cover what the user currently uses to live.

At block 208, embodiments of the invention further include determining estimated rates of return for the assets that provide returns. In some embodiments, the assets may include estimated rates of returns such that not only are the disbursements used in determining the retirement score, but the principal and growth of the principal over time may be used in determining the retirement score.

At block 210, embodiments of the invention further include determining financial behavior of the user, wherein the financial behavior comprises at least one of a spending behavior, investment behavior, and savings behavior. In one aspect, determining financial behavior of the user may include determining a spending pattern, investment pattern, and savings pattern of the user over a predetermined past period of time. In one aspect, determining the financial behavior of the user is based on at least the user profile. In this regard, the system may be configured to generate one or more predetermined questions to enable the user to provide additional information regarding the user's financial behavior to the system. In one aspect, the predetermined questions may enable the system to receive information associated with the personality, values, opinions, attitudes, interests, lifestyles, or the like of the user.

At block 212, embodiments of the invention further include calculating a retirement score for the user based on one or more parameters, wherein the one or more parameters comprise at least the asset values, the liability values, the user profile, the estimated rates of return, and the financial behavior of the user, wherein the retirement score indicates the user's preparedness for retirement at a future predetermined date, wherein the future predetermined date is selected by the user. At block 214, embodiments of the invention further include displaying the retirement score on a retirement planning interface on a user device.

As discussed above, the retirement score is calculated based on one or more parameters. Some of these parameters (e.g., fund in-flows and fund out-flows) may include continuously varying values which when used to calculate the retirement score may not result in the most accurate representation of the retirement score. In this regard, the system may be configured to represent the retirement score according to a confidence score. The confidence score may be represented in any format including, but not limited to, a percentage, a ranking, a numerical value, or the like. In doing so, the user may be able to gauge the accuracy of the retirement score. For example, a retirement score of 40/100 with a confidence score of 50% may indicate that the retirement score may not be the most accurate representation of the retirement score with a confidence level of only 50%. A lower confidence score may indicate that the data (one or more parameters) used in the calculation of the retirement score are either incomplete or dated. The enables the user to review the information initially provided and update the information to retrieve an accurate representation of the retirement score.

In some embodiments, the system may be configured to receive a desired future predetermined date for retirement from the user through the retirement planning interface. In response, the system may be configured to recalculate a new retirement score for the user based on the desired future predetermined date for retirement. In response to calculating a new retirement score, the system may be configured to display the new retirement score and the desired future predetermined date on the user interface of the user device.

In some embodiments, the system may be configured to compare the retirement score of the user with an average retirement score associated with one or more users with substantially similar one or more parameters as that of the user to determine whether the retirement score of the user is high or low. For example, the user who is 25 years old may not save as much as other older users, but may be saving more than his/her peers with a substantially similar user profile. In this case, the user's retirement score may be low compared to the retirement scores of older individuals but may be high when compared to peers with a substantially similar user profile.

In some embodiments, the system may be configured to determine that the user has a low retirement score based on at comparing the retirement score of the user with an average retirement score associated with one or more users with substantially similar one or more parameters as that of the user. In response, the system may initiate a presentation of one or more tips on the retirement planning interface on the user device to enable the user to improve the low retirement score to within the average retirement score associated with the one or more users. In one aspect, the one or more tips may include refinancing, a free consultation with a financial advisor, or the like.

In some embodiments, the system may be configured to determine that the user has a high retirement score based on at least comparing the retirement score of the user with an average retirement score associated with the one or more users with substantially similar one or more parameters as that of the user. In response, the system may be configured to initiate a presentation of one or more services specific to the user on the retirement planning interface on the user device, wherein the one or more user specific services comprises a financial planning service.

In some embodiments, the system may be configured to receive one or more parameters associated with one or more users in a household of the user. In this regard, the one or more users in the household of the user may be financial institution customers. In response, determine a retirement score for the household based on at least the one or more parameters received from the one or more users in a household of the user and the retirement score of the user. In one aspect, the system may be configured to retrieve information associated with the one or more users in the household from one or more financial institution accounts of each of the one or more users. For example, two or more users in a household may plan for retirement individually based on their individual assets and finances. In such cases, the system may be configured to aggregate the information associated with the two or more users in the household in a central location to enable the system to calculate a retirement score for the entire household.

In one aspect, the system may be configured to track the retirement score of the user over a predetermined past time period. In this regard, the system may be configured to enable the user to select the predetermined past time period. And in response, the system may initiate presentation of the retirement score of the user relative to a retirement score associated with one or more users over the predetermined past time period, wherein the one or more users are determined to have a substantially similar user profile as that of the user.

In some embodiments, the retirement score may be used by entities such as lenders (banks and credit card companies) to evaluate potential risk posed by lending funds to the user. In this regard, the retirement score may be used in conjunction with other credit scores (e.g. FICO score) to evaluate such risk.

FIG. 3 illustrates a high level process flow for determining a projected retirement score based on linking user profiles 300. As shown in block 305, embodiments of the invention further include receiving projected retirement information of a first user comprising a user profile of the first user. The user profile may be associated with a financial institution, a financial advisor or retirement planner, and an insurance provider. The profile may include information related to assets and liabilities of the first user, wherein the assets include illiquid assets and liquid assets as explained in defined in other portions of the specification.

The user profile describes a lifestyle of the user. In this regard, the system may be configured to determine the user profile based on at least one or more past transactions of the user, a geographic location of the user, an income level, an amount of outgoing funds, asset values, liability values, asset types, spending habits, saving habits or the like as explained in other portions of this specification. In one aspect, the user profile includes at least information identifying the first user. In other embodiments, the system may be configured to allow the user to update the user profile of the first user.

At block 310, embodiments of the invention further include generating a projected retirement score based on the projected retirement information of the first user. In some embodiments, the system calculates the projected retirement score based at least in part on an amount of savings of the user for retirement, an amount of savings the user needs during retirement, and a number of years the user has to get ready for retirement. With respect to the amount of savings of the user for retirement, the system may identify savings and other retirement accounts from the user profile. The system may automatically determine a retirement account based on the type of account (e.g. 401K). In other embodiments, the user may designate an account as a retirement account. Where the account is an interest bearing account, the system may calculate at least a future amount based on the system collecting and compounding interest. For example, the user may have designated a savings account as a retirement account that generates 1% per annum. The system further determines that the user contributes $100 per month into the savings account. The system may determine an available amount of funds at a future period of time based on such information. The future period of time may coincide with the retirement of the user. Where the account is an investment account, the system may determine based on market information, an amount each investment vehicle in account will be worth at a future period of time. In addition to account information, the system may determine that the user maintains an interest of ownership in real property. With respect to the user's ownership in real property, the system may determine based on historic market information of the property, a value of the property at a future period of time. The system may further determine whether the property generates an income (e.g. rent, timber sale, farm product). The system may valuate the land based on the generated income of the property. In other embodiments, the system may determine an amount the user will likely earn prior to retirement and an amount the user will save from the earnings for retirement. The system may view employment history of the user to determine a current salary of the user. Such employment history may include the occupation of the user. Additionally, the system may determine an expected increase in the salary of the user over a period of time prior to retirement. For example, the system may determine that the user is a teacher and paid a salary of $X.XX per annum. The user has been teaching for 5 years. The system may determine based on employment data that the salary of the user will increase 7% per year until the user retires. The system may determine an expected amount that the user will likely save for retirement from the increase in salary. In some embodiments, the system may determine that the user will receive benefits after retirement such as military and government benefits. These benefits will be included into a post-retirement income that will offset any amount the user may require to save for retirement.

In other embodiments, the system may determine that the user may want to partially retire and continue to receive an additional post-retirement income. In other embodiments, the system may further determine the user wants to start a business for retirement. The system may determine the amount of money the user needs to start the business and calculate the projected retirement score based on the needs to start the business. The system may further determine an expected salary from the business.

With respect to the amount of savings the user needs during retirement, the system may determine the cost of living for an area in which the user lives. Cost of living may include necessities such as groceries, rent, and insurance. Cost of living may also include other financial factors such as money for vacations, club memberships and such. In other embodiments, the system may determine based on past financial history of the user, the spending habits of the user to determine the amount the user needs during retirement. When the system determines past spending habits, the system may further determine whether the user plans to live a similar life style to which the user has lived prior to retirement. Such information may be gathered as a result of sending a questionnaire to the user. The information may further be received from a third-party consultant of the user (e.g. financial planner). In one example, the system may determine that the user has a property worth $X.XX amount of dollars which the user uses a primary residence. The system petitions the user whether the user intends to retain the property as a retirement home. If the user answers that the user intends to sell the property and rent a smaller property, the system would calculate the amount from a sale of the property and the amount the user would need for rent. The system may also determine insurance for the user during retirement. When the system determines that the user will receive a post-retirement income, the system may use such income to determine the amount the user needs to save after retirement.

With respect to amount of time the user has to save for retirement, the system may determine the current age of the user and the age at which the user would like to retire or partially retire. In other embodiments, the projected retirement score may include an age of retirement for a given score. For example, after the system receives the user profile and determines an amount the user would need for retirement, the system may determine different retirement ages for the user. The ages may be determined arbitrarily (e.g. the age of the user ten years in the future up until the user is a certain age), or the ages may be supplied by the user. After the retirement ages have been determined, the system may further calculate a projected retirement score for each age. For example, the user may supply a retirement age of 40, 45, 50, 55, and 60. Based on the both the amount the user has saved for retirement and the need of the user during retirement, the system may determine the projected retirement score for each age. Such score determines the readiness of the user to retire when the given age is achieved. In another embodiment, the projected retirement score is an age at which the user may retire.

In other embodiments, the system may determine different factors that may lower the projected retirement score of the user based on the financial information. Such factors may include paying off a higher interest loan faster or consolidating debt. The system may calculate a possible projected retirement score if the user corrects the factors. Additionally, the system may receive an indication that the user fulfilled the factors and update the projected retirement score accordingly.

At block 315, embodiments of the invention further demonstrates receiving a request to link a user profile of a second user to the user profile of the first user. The user profile of the second user is similar to the user profile in the first user in the information that is contains and how it can be created and edited. The system may be configured to receive the request to link the user profile of the first user to the user profile of the second user from a computing device associated with at least one of the first user or the second user. In other embodiments, the system may be configured to suggest a link between the first user and the second user. In some embodiments, the suggesting the link may be based on a relationship between the first user and the second user. Such a relationship may include but is not limited to marital relations, living relations, agreements, and other familial relations. The system may provide at least the first user or the second user to supply such relationship information via a computing device of the user. Additionally, the system may be configured to determine accounts of the first user that are commonly owned or managed by the second user. For example, the system may determine that the first user manages a checking account and a savings account. The system may further determine that the checking account and the savings account are also managed by the second user. Based on such a determination the system may suggest a link to the first or second user.

After receiving the request to link the user profiles, the system may be configured to authenticate the request. Such authentication may be based at least in part on authentication credentials of the first user. In other embodiments, the authentication credentials may be based in part on authentication credentials of the second user. While in yet other embodiments, the authentication credentials are based on authentication credentials of both the first user and the second user. Based on receiving the request to link the user profile of the second user to the user profile of the first user, the system may actually create a link between the different user profiles.

At block 320, embodiments of the invention further include demonstrates receive projected retirement information of the second user based on receiving the request to link the second user to the first user. Such information may be similar that information received on behalf of the first user in block 305. After receiving the information for the second user, the system may combine the information of the first user with the information of the second user to obtain a combined user profile. In combining the user profiles, the system may be configured to determine duplicity of information. For example, the system may determine that the first user is liable for the same mortgage for which the second user would be liable. The system may remove the duplicity of information based on making such a determination.

At block 325, embodiments of the invention further include demonstrates updating the projected retirement score based on the combined information of the first and second user and the first and second profiles. Based on the combined user profile and combined information, the system may update the projected retirement score. In some embodiments, based on the system updating the projected retirement score, the system may determine the difference between the original projected retirement score and the updated projected retirement score. Such information may be informative to the user as to the amount and in what direction the score changed.

In some embodiments of the invention, the system may recognize that the first user or the second user may have a life event occur at a future period of time. Additionally, the system might determine that the first user and the second user will experience the life event together at the future period of time. For example, where the first user and the second user have a child, the system might determine the age of the child and determine an approximate time at which the child will attend college. In some embodiments, the system may recognize that the first or the second user will experience the life event based on the financial information received for the first user and the second user. In other embodiments, the system may prompt the user to enter in information related to a future life event. For example, the system may prompt a user to enter information stating that the user is interested in purchasing a home. Where the system has created a link between the first user and the second user, when the system recognizes a life event for the first or second user, the system may automatically apply the life event to the other user.

After recognizing the life even of at least the first user or the second user, the system may further update the projected retirement score based on the life event. In updating the projected retirement score, based on the life event, the system may determine how the life even would impact the retirement of at least the first user and the second user. For example, the system may recognize that the first user and the second user are anticipating buying a house. The system may collect information related to the house (location, property value, insurance, taxes, down payment, mortgage interest rate), and based on the information related to the house, the system may determine that the amount of money the first user and the second user would put towards the house over the life of a mortgage on the home. Using this information, the system may determine that the first user and the second user would have less money to put towards a shared retirement fund. However, the system may further determine an expected appreciation of the home over a period of time and update the projected retirement score based on the excepted appreciation of the home over the period of time.

In calculating the projected retirement score of the first user and the second user, the system may use a confidence factor or confidence score (as defined herein), in calculating the projected retirement score. Such confidence score may be based on information related to the first user and the second user individually or to the first user and the second user collectively. Where the information relates to the first user and the second user collectively, the system may analyze information about the relationship between the first user and the second user. For example, the system may determine that the first user and the second user are planning on being partners in a business upon retirement of the first user and the second user. The system may receive information about the business relationship between the first user and the second user and may further receive information relating to the business. When using the confidence score to calculate the projected retirement score, the system may create a range in place of an actual score. The range may include a best case and worst case scenario based on the information that the system currently has in place.

In some embodiments of the invention, the system may determine that the first user and the second user are in different stages of life. For example, the system may determine that the first user is 30 years from retirement while the second user is 2 years from retirement. The system may determine that the second user will be dependent upon the first user for funds when the second user retires. The system may update the projected retirement score based on such information. Additionally, the system could generate a relationship score apart from a retirement score of the first user and a retirement score of the second user. The relationship score would detail the readiness of a life event of the relationship (e.g. retirement of the second user). Based on the relationship retirement score, the system may update the individual retirement scores of the first user and the second user. A given user may have multiple relationships with different other users where each of the relationships is afforded a different relationship score. The projected retirement score of the user may be based on the individual relationship scores from each relationship. For example, User A may have a relationship with User B to whom User A is married. User A may also have a relationship with User C, who is the child of User A. User A may also have a relationship with User D, who is a business partner of User A. Each of the relationships is afforded a different relationship score based on financial and non-financial information between each of the users. However, the relationship score may be parsed to only include information that is essential to the relationship (e.g. for the relationship for User A and User D, a financial account owned by the partnership). The system may prompt the user to assign to which relationship the system should apply particular financial and non-financial information. In other embodiments, the system may automatically apply the information based on each user supplying the information. For example, the system may determine that both User A and User B have supplied the same information related to a bank account shared between User A and User B.

In other embodiments of the invention, after the system has created the link between the first user and the second user, the system may receive a request to delink the first user with the second user. Such delinking may be the result of a life event (e.g. death), or may be automatically determined (e.g. predetermined end of a partnership).

At block 330, embodiments of the invention further include demonstrates communicating the projected retirement score. In some embodiments, the score may be communicated to at least the first user and the second user. In other embodiments, the system may further communicate the difference between the original projected retirement score and the updated projected retirement score.

FIG. 4A illustrates utilizing the determined retirement score for benefit qualification determination, in accordance with some embodiments of the invention. As illustrated in block 402, the process 400 is initiated by retrieving the retirement score calculated for the user. The retirement score is retrieved from the system associated with the retirement planning interface. As discussing in further detail above, the retirement planning score is calculated based on a determination of a financial behavior of the user, wherein the financial behavior comprises at least one of a spending behavior, investment behavior, and savings behavior. In one aspect, determining financial behavior of the user may include determining a spending pattern, investment pattern, and savings pattern of the user over a predetermined past period of time. In one aspect, determining the financial behavior of the user is associated with the user profile. Once the financial behavior is determined, the system may calculate a retirement score for the user based on one or more parameters, wherein the one or more parameters comprise at least the asset values, the liability values, the user profile, the estimated rates of return, and the financial behavior of the user. The retirement score indicates the user's preparedness for retirement at a future predetermined date, wherein the future predetermined date is selected by the user.

Next, as illustrated in block 404, the process 400 continues by parsing out the retrieved retirement score into its component parts. As such, the system may parse out a score for each of the one or more parameters used to determine the overall retirement score. In this way, a score may be reflected for each of the asset values, the liability values, the user profile, the estimated rates of return, and the financial behavior of the user. Furthermore, the system may parse out the retirement score based on life events, as described in further detail above. The system distributes a score for each of the parsed component parts of the retrieved retirement score for the user.

Once the components of the retirement score have been parsed into separate scores for each component, the process 400 continues by distributing the parsed retirement score, as illustrated in block 406. The component parts as well as the overall retirement score for the user may be distributed among the financial institution for association with the user. The component retirement score comprise a value corresponding to at least the asset values, liability values, the user profile, estimated rates of return, and the financial behavior of the user. While the overall retirement score indicates the user's preparedness for retirement at a future predetermined date, the component retirement score assesses a user's preparedness for each of the components at a current state. As such, the system may identify one or more components of weakness or strength of a user during retirement planning and wealth accumulation for retirement. The component parts may include scores associated with spending pattern, investment pattern, savings pattern, asset values, liability values, estimated rates of return, and the like. As such, the system may parse out the overall retirement score into its component parts via algorithmic back calculations of the generated scoring. The component part scoring may provide the system with item level scores for the user that may be distributed among groups of a financial institution to provide the user with benefits that may not normally be provided to the user based on age, investments, or the like.

Next, as illustrated in block 408, the process 400 continues by identifying benefits available to the user based on the retirement score in combination with one or more component retirement scores. As such, the system may identify benefits that the user may qualify for based on the scores. These benefits may be ones that the user would not normally qualify for, such as reduced assessments on accounts, free advisor meetings, various privileged accounts, interest rate reductions, or the like. Typically, benefits such as these are reserved for customers with large assets with a financial institution, older customers, and/or stability with the financial institution for a long duration. However, the retirement score and component scores may illustrate a propensity of a user for good savings behaviors or predicted financial health at a future date. For example, a the retirement score and/or component scores may be used to provide a user products with reduced assessment or for free advisor meetings even if the user is young and may not have large assets savings for retirement, but because the user may illustrate positive savings behaviors as reflected in the retirement score or component of the retirement score. As such, the user may be identified as a candidate that will likely have positive retirement position in the future.

In some embodiments, the system may also determine individuals associated with the user and link those individuals' retirement scores to the user. Furthermore, in some embodiments, a user may elect to share his/her score with another individual. As such, increasing or decreasing the user retirement score for benefit approval and authorization. It may be determined that an individual is associated with the user based on a relationship with the user wherein finances may be shared or expected to be shared between one or more individuals and the user. In other embodiments, an individual may be linked to a user based on manual input from the user or individual.

Finally, as illustrated in block 410, the process 400 continues by presenting the benefits available to the user based on the retirement score and/or the component retirement scores. The presentation of benefits, which are directed to financial institution products, are presented to the user via an interface.

Furthermore, in some embodiments, the retirement score may be used in replace of or in association with a financial assessment score, such as a credit score, for third party financial determinations associated with a user. As such, the system may provide secure authorization and access to third parties requesting a retirement score in association with a financial assessment score. The retirement scores may be reported along with the user's credit score for reporting agencies. The retirement score may be utilized by third parties, such as other financial institutions, or reporting agencies that have authorized access to the scores, for financial product determinations for a user. A monitoring system may be associated with the system to determine authorized requests for the retirement score for product determination.

FIG. 4B illustrates a process flow for reporting and utilizing the retirement score for third party presentment, in accordance with some embodiments of the invention. The process 401 is initiated by compiling the retirement scores calculated for the user, as illustrated in block 403. As such, the system compiles the scores that were calculated from above. Next, the system may, in some embodiments, retrieve user financial assessment scores, as illustrated in block 405. A user financial assessment score may include any score that is utilized by third parties for financial products as an assessment of financials, such as a credit score or the like.

Next, as illustrated in block 407, the process 401 continues by combining and associating the user retirement score in conjunction with the financial assessment scores. As such, for each user, the circuitry associated with the system may identify and combine the newly created retirement score with one or more financial assessment scores associated with the user. Once the scores are associated with each other, the scores are stored together in the database. The scores may be regularly updated as needed in the database.

As illustrated in block 409, the process 401 continues by reporting the retirement score and financial assessment score to a reporting agency and monitoring system. The monitoring system is an internal device that is associated with the system. The scores may be provided to the reporting agency based on authorization and approval for access to the scores. As illustrated in block 411, next the monitoring system associated with the system may receive a request for distribution of the retirement score with the assessment score. This request is received at the monitoring system and received from an outside third party. Furthermore, the request may include an authorization code that may authorize the third party to receive the scores. As such, the monitoring system may receive the request identifying an individual, a score requested, and an authorization code that authorizes the distribution of the score to the third party of the request. The monitoring system may identify the user associated with the request ad confirm the authorization code. The authorization code may be user specific and/or requestor specific.

Next, as illustrated in block 413, the monitoring system may distribute the retirement score with financial assessment score based on the third party request and authorization. As such, through the network the monitoring system may distribute the scores to a third party server securely. In some embodiments, the monitoring system may encrypt the scores and store the encrypted stat on the third party server. The monitoring system may authorize or provide decryption to the third party server to gain access to the scores associated therewith. Finally, as illustrated in block 415, the process 401 is completed by utilizing the combined retirement score in association with the financial assessment score for product implementation for the user. As such, in some embodiments, the monitoring system may provide the retirement score in combination with the financial assessment score to a third party. The third party may utilize the combination of scores to determine user qualifications for a financial product or funding. In other embodiments, the system may utilize the retirement score in combination with the financial assessment score for the financial institution determination of qualification for discounts, financial products, funding, or the like.

FIG. 5A illustrates a high level process flow for optimization of a user retirement score 500, in accordance with one embodiment of the invention. In this way, the system may provide tips to improve the retirement score to the user and also provide information as to how the improvements to the score will be achieved. For example, the system may indicate that the user is losing an amount of funds by not taking a particular action with respect to retirement planning. The system may suggest that the user should move to a different location, continue to work in on or in retirement, or the like. Moreover, the retirement score may be illustrated over time and improvements may be suggested illustrating how the score may be improved by utilizing financial institution products provided via the system. For example, the user's retirement score may be high in year 1, drop to a lower number in year 2 because of a large asset purchase, such as a home, or the like. The system may provide tips or products to the user to help improve the score and/or return the score to a desired level. The user may allow the system to automatically take action with respect to the user's assets in order to improve the retirement score. In this way, for example, the system may automatically transfer excess money from a checking account to a self-directed investment account. In yet other embodiments of the invention, the system may create shell accounts for the user that allows the system to sweep funds to various accounts for retirement planning. Moreover, the system may provide reverse looking views to illustrate if the recommendations or tips provided by the system resulted in or would have resulted in an improved retirement score and/or increased value of the assets.

As illustrated in block 502, the process 500 is initiated by retrieving the created retirement score for a user. The retirement score is retrieved from the system associated with the retirement planning interface. As discussing in further detail above, the retirement planning score is calculated based on a determination of a financial behavior of the user, wherein the financial behavior comprises at least one of a spending behavior, investment behavior, and savings behavior. In one aspect, determining financial behavior of the user may include determining a spending pattern, investment pattern, and savings pattern of the user over a predetermined past period of time. In one aspect, determining the financial behavior of the user is associated with the user profile. Once the financial behavior is determined, the system may calculate a retirement score for the user based on one or more parameters, wherein the one or more parameters comprise at least the asset values, the liability values, the user profile, the estimated rates of return, and the financial behavior of the user. The retirement score indicates the user's preparedness for retirement at a future predetermined date, wherein the future predetermined date is selected by the user.

Once the created retirement score is retrieved, the system may identify user location and financial products currently held by the user, as illustrated in block 504. The location may include the primary geographic location the user resides and/or spends an amount of time in. In this way, the system may identify and create a financial analysis of the geographic location, recognizing that various geographic locations have varying cost associated therewith. Furthermore, the system may identify financial institution products associated with the user. These may include financial accounts such as savings accounts, checking accounts, money market accounts, or the like. Furthermore, this may include any financial products the user has directed to financial savings for retirement.

Next, as illustrated in block 506, the process continues by reviewing the user financial products and identifying user spend. Once reviewed, the system may identify financial products that, if implemented by the user, would improve the user's retirement score, as illustrated in block 508. These financial products may include financial accounts, insurance, investment options, or the like. The products may be identified based on each individual's needs. Thus, each identified product is tailored to the individual it is generated for. The financial products may be products that the user qualifies for based on the retirement score. The determination of the appropriate financial products may be based on inputting the financial product into a generation system or recreation scenario system. In this way, the system may input that financial product at a time in the past into the user's retirement score. As such, using an interface, the system may determine if the user's retirement score is positively or negatively affected by the implementation of the product. The system may input, into a simulation, the financial product at one or more times throughout the history of the user and subsequently generate a current retirement score that incorporates the added product. This newly generated retirement score may be compared to the user's current retirement score to see if the simulated impact of the financial product may positively or negatively impact the user's retirement score.

As illustrated in block 510, the user spend and location aspects are identified for retirement score improvements. In some embodiments, user spend may be identified. User spend may include daily, weekly, monthly, or yearly transactions of the user. As such, the system may determine a user spend or a pattern of transactions for a given time frame. The system may also determine a location of the user and assess the expenses of living at that geographic location.

As such, the system may have identified financial products that, if implemented, would improve the user's retirement score, the system has identified user spend, and the system has identified the user location. Using this data the system may identify recommendations for the user to implement to aid in improving his/her retirement score in the future. As part of this improvement, as illustrated in block 512, the system may automatically shift the user into an appropriate financial product for retirement score improvement. As such, based on the identified financial products that, if implemented, would improve the user's retirement score, the identified user spend, and the identified the user location, the system may automatically shift the user into an appropriate financial product. Thus, once a product is identified, such as an account, insurance, investment, or the like that will improve the user's retirement score, the system may automatically shift the user into that product. As such, the user may not need to enroll or otherwise authenticate the shift, instead the system may identify the product and automatically shift the user into the product based on the improvement the product creates for the user's retirement score.

Finally, as illustrated in block 514, the process 500 ends by presenting the user with other recommendations for retirement score improvement and implementation of the recommendations.

FIG. 5B illustrates a process flow for reverse review of retirement score calculations based on recommendations 501, in accordance with one or more embodiments of the invention. As illustrated in block 503, the process is initiated by retrieving the created retirement score. The retirement score is retrieved from the system associated with the retirement planning interface. As discussing in further detail above, the retirement planning score is calculated based on a determination of a financial behavior of the user, wherein the financial behavior comprises at least one of a spending behavior, investment behavior, and savings behavior. In one aspect, determining financial behavior of the user may include determining a spending pattern, investment pattern, and savings pattern of the user over a predetermined past period of time. In one aspect, determining the financial behavior of the user is associated with the user profile. Once the financial behavior is determined, the system may calculate a retirement score for the user based on one or more parameters, wherein the one or more parameters comprise at least the asset values, the liability values, the user profile, the estimated rates of return, and the financial behavior of the user. The retirement score indicates the user's preparedness for retirement at a future predetermined date, wherein the future predetermined date is selected by the user.

Next, as illustrated in block 505, the process 501 retrieves the determined recommendations for retirement score improvement. These recommendations include location changes, financial product changes, or the like. Next, as illustrated in block 507, the process 501 continues by retrieving historic retirement score data for a user. The retirement score for a user typically changes and is fluid based on financial impact to the user's retirement planning financials. As such, the system may retrieve the historic retirement score data for a user at several points in the past to reflect the changes in the retirement score. These historic retirement scores may be presented to a user via an interface, as illustrated in block 509. This may illustrate a backward looking insight into the user's retirement score history and identification of trends associated with the score.

As illustrated in block 511 the system may augment the historic retirement score data with the recommendations at various times in the past. Thus, this augmentation may change the graphical data of the user's retirement score today. In this way, the system may augment historical data for retirement to illustrate if those recommended steps were taken at that historical time, then the impact of those steps will be displayed in the augmented retirement score.

Finally, as illustrated in block 513, the system may illustrate the recommendation effect on the user's current retirement score to illustrate what the user's score would look like now had the user implemented the recommendation at that time in the past.

Using the augmented retirement score, the system may present a graphical representation of the user's past, present, and future retirement score. The graph may be selectable by the user at one or more different time points on the retirement score graph from past to present to future along a timeline. At each time point, the user may select the graph to illustrate the one or more life events that effected the score at that point. That point may be in the future, past, or present. This way, the user may identify the major events at any give them that effect a retirement score significantly.

Finally, the augmented retirement score may have a confidence level calculated associated with that augmented score. The confidence score provides a confidence that the augmented score is accurate based on the data provided by the user. Furthermore, the confidence score may take into account life events that may or may not have occurred for the user, thus ensuring no false positives of scoring.

FIG. 6 illustrates a high level process flow for assessing impact of life events on retirement planning 600. As shown in block 602, embodiments of the invention further include calculating a retirement score (as described herein) for the user based on at least the one or more parameters, wherein the retirement score indicates the user's preparedness for retirement at a future predetermined date, wherein the future predetermined date is selected by the user. The system may be configured then to initiate a presentation of an event user interface to the user, wherein the event user interface comprises at least selectable life event options for one or more life events, as shown in block 604.

In some embodiments, the selectable life event options may include one or more life events that could occur for the user. In this regard, the selectable life events may include, but are not limited to paying for a dependent to go to college, purchasing a house, saving for retirement, planning a wedding, planning a trip, or the like.

As shown in block 606, embodiments of the invention further include receiving, via the event user interface, a user selection of at least one life event from the one or more life events. In response, the system may be configured to initiate presentation of an event information user interface to the user to enable the user to input life event information associated with the at least one life event selected by the user, as shown in block 608. In one aspect, the event information interface is provided on the user device and include information associated with the at least one life event selected by the user. In some embodiments, the event information may include one or more predefined selectable options for the user. For example, if the user selects paying for a dependent to go to college, the corresponding event information may include a drop-down list of one or more colleges, fee structure associated with the college, cost of living associated with the city in which the college is located, payment methods, federal and/or private loans/scholarships available, or the like. If the user selects purchasing a house as one of the life events, the corresponding event information may include a payment method, an amount of down payment that the user is willing to apply towards the purchase of the house, an interest rate associated with payment method, or the like.

In another aspect, the event information may include one or more predefined questions associated with the selected life event. In this regard, the system may be configured to enable the user to provide information associated with the one or more predefined questions. In another aspect, the event information may enable the user to customize the event information user interface by creating additional options to enter selective information. In such cases, the system may be configured to enable the user to create a customized event information option to enable the user to enter selective information.

In some embodiments, the system may be configured to analyze the one or more life events selected by the user and provide recommendations and tips to enable the user to better achieve the selected life event. For example, if the selected life event is purchasing a house, the system may be configured to provide recommendations related to one or more preferred insurance companies, service contractors, or the like.

As shown in block 610, embodiments of the invention further include retrieving information associated with the at least one life event selected by the user from substantially similar life events selected by one or more users determined to have a substantially similar user profile as that of the user. In this regard, the system may be configured to determine one or more life events selected by one or more users with substantially similar profiles as the user. The system may then retrieve information associated with the life events selected by the one or more users based on at least determining that the life event selected by the user is substantially similar to the life event selected by the one or more users with substantially similar profiles as the user. For example, the life event selected by the one or more users may be paying for college. In another example, the life event selected by the one or more users may be purchasing a house.

As shown in block 612, embodiments of the invention further include calculating a life event score associated with the at least one life event selected by the user based on at least the retirement score, the received life event information and the information retrieved from the substantially similar life events selected by the one or more users with substantially similar profiles as the user. In some embodiments, even though the life event may be the same, the information associated with the event may be distinct. In this regard, some users may select attending college for an undergraduate degree; some users may select attending college for a graduate degree. In another example, the life event may include purchasing a house. However, the information such as location of the house, size, amount of down payment, or the like may be different for each user. In some embodiments, the system may be configured to assign weights to information associated with one or more life events selected by one or more users with substantially similar profiles as the user for information retrieval. In this regard, the system may assign predetermined weights for predetermined information associated with the one or more life events. In one aspect, assigning predetermined weights may be based on at least comparing event information associated with the one or more life events selected by the one or more users with substantially similar profiles to determine a match. For example, if the user wishes to purchase a house in Hawaii, the system may be configured to compare the location of properties with substantially similar size purchased by the one or more users with substantially similar profiles as that of the user based on a surrounding geographic area, locations with similar cost of living, taxes, or the like. In this regard, matching event information may be assigned a higher weight. For example, if the user wishes to attend college at a public university in a college town, the system may assign a higher weight to information selected by the one or more users with substantially similar profiles as the user who previously selected a life event to attend college at a public university. In contrast, the system may assign a lower weight to information selected by the one or more users with substantially similar profiles as the user who previously selected a life event to attend college at a private university in a city. Accordingly, the system may be configured to calculate a life event score for each life event selected by the user.

As shown in block 614, embodiments of the invention further include initiating a presentation of a payment user interface to the user, wherein the payment user interface is provided on the user device and comprises the calculated life event score.

In some embodiments, the system may be configured to determine that the user has selected a single life event from the selectable life event options for one or more life events. In response, the system may determine a payment disbursement plan to enable the user to pay for the single life event selected by the user based on at least the life event score associated with the single life event selected by the user. In some embodiments, the disbursement plan comprises a percentage allocation of funds from the one or more financial institution accounts of the user to be applied towards the single life style event selected by the user, and minimizing any penalties associated with using the funds associated with the user's assets. In one aspect, the disbursement plan may enable the user to either apply funds towards the life event itself or apply funds towards a saving initiative for the life event.

In some other embodiments, the system may be configured to determine that the user has selected multiple life events from the selectable life event options for one or more life events. In response, the system may determine a payment disbursement plan to enable the user to pay for each of the multiple life events selected by the user based on at least the life event score associated with each of the multiple life events selected by the user. In one aspect, the disbursement plan comprises a percentage allocation of funds from the one or more financial institution accounts of the user to be applied towards each of the multiple life events selected by the user. In this regard, the funds are applied towards at least a percentage of payment for each of the multiple life events selected by the user, and minimizing any penalties associated with using the funds associated with the user's assets.

In some embodiments, the system may determine the life style score associated with each of the one or more life style events based on at least the information retrieved from the substantially similar life events selected by the one or more users. In response, determine that the user is ready to begin allocating funds towards at least one of the one or more life style events based on at least the user profile and the determined life style score. In response to determining that the user is ready, the system may be configured to recommend that the user allocate a percentage of funds from the one or more financial institution accounts of the user to be applied towards the one or more life events. For example, if the user has selected three life events, the system may be configured to determine a payment disbursement plan and recommend that the user apply 3% of funds from the user's financial institution accounts towards saving of the first life event, 5% of funds from the user's financial institution accounts towards saving for the second life event, and 2% of funds from the user's financial institution accounts towards saving for the third life event.

In some embodiments, the system may be configured to enable the user to adjust the percentage allocation of the amount from the one or more financial institution accounts of the user. In response to determining a percentage allocation, the system may be configured to enable the user to execute the payment disbursement plan.

FIG. 7A illustrates an exemplary retirement planning user interface 700 in accordance with an embodiment of the invention. As shown, the retirement planning interface includes selectable options for one or more life events 702, a user profile 704, a current retirement score 706, and a cancel option 708.

FIG. 7B illustrates an exemplary event information user interface 750 in accordance with an embodiment of the invention. As shown, the event information user interface 750 includes the selected life event 752, life event information 754 associated with the selected life event 752, a user profile 704, a retirement score 706, and a cancel option 708.

FIG. 8 illustrates a high level process flow for creating a social network group membership for a user based on a projected retirement score of the user 800. As shown in block 805, embodiments of the invention include creating a social network group. The social network group may be hosted on a server or other computing device maintained by a financial institution or by another third party. Typically, the group has limitations for admitting members. In one embodiment, the limitations may be based on financial information with respect to a person seeking such membership. More specifically, the membership may be based on a projected retirement score of a user as is defined in block 820 and a projected group retirement score range as is defined in block 825.

After the social network group has been created, the system may be configured to receive requests to join the social network group as defined in block 810. The system may cause a personal computing device of the user to display an enrollment form to join the social network group. The user may fill out the form and submit such a form to the system for processing. Upon receiving the form, the system may begin the enrollment process and determine whether the user is eligible to join the social network group. In other embodiments, the system may be configured to determine from a list, users that would be eligible to join the social network group based on the financial information for each user. After determining the users that would be eligible to join the social network group based on the financial information, the system may communicate an invitation to such users to join the social network group.

As described in block 815, as part of the enrollment and membership determination process, the system receives financial information for the user. The financial information may relate to assets and liabilities of the user, wherein the assets include illiquid assets and liquid assets. The user's assets may include but are not limited to checking accounts, savings accounts, investment accounts (e.g., with regular disbursements and penalties for principal withdrawals, or self-directed accounts that more liquid without penalties), annuity accounts (e.g., social security, claim awards, reverse mortgages, or the like), insurances benefit accounts (e.g., one time or reoccurring), property owned by the user (e.g., investment property, rental property, or the like), or other like assets that may provide regular or semi-regular recurring payments, assets that are or are similar to cash accounts, or assets that need to be sold in order to realize cash values of the assets. In some embodiments the assets may be illiquid (e.g., have penalties or may take time to convert into cash) or may be liquid (e.g., can be converted to cash in a couple of days without penalty). In one aspect, the process flow includes determining a user's asset values (e.g., balances of the account, current or estimated future fair market values of the property, or the like) and liability values (e.g., amount owed, or the like). The user's liabilities may include a mortgage, long and short term debit, payments owed on other personal property or legal judgments against the user, or the like). In some embodiments all of the assets and liabilities are determined in order to get an idea of what the values of the assets and liabilities are in order to determine how long the inflows and outflows for the user may last. In one aspect, the financial information may further include at least information identifying the user. In other embodiments, the financial information may relate to health information of the user, insurance information of the user, and employment information of the user.

At block 820, embodiments of the invention further include generating a projected retirement score based on the projected retirement information of the user. In some embodiments, the system calculates the projected retirement score based at least in part on an amount of savings of the user for retirement, an amount of savings the user needs during retirement, and a number of years the user has to get ready for retirement. With respect to the amount of savings of the user for retirement, the system may identify savings and other retirement accounts from the user profile. The system may automatically determine a retirement account based on the type of account (e.g. 401K). In other embodiments, the user may designate an account as a retirement account. Where the account is an interest bearing account, the system may calculate at least a future amount based on the system collecting and compounding interest. For example, the user may have designated a savings account as a retirement account that generates 1% per annum. The system further determines that the user contributes $100 per month into the savings account. The system may determine an available amount of funds at a future period of time based on such information. The future period of time may coincide with the retirement of the user. Where the account is an investment account, the system may determine based on market information, an amount each investment vehicle in account will be worth at a future period of time. In addition to account information, the system may determine that the user maintains an interest of ownership in real property. With respect to the user's ownership in real property, the system may determine based on historic market information of the property, a value of the property at a future period of time. The system may further determine whether the property generates an income (e.g. rent, timber sale, farm product). The system may valuate the land based on the generated income of the property. In other embodiments, the system may determine an amount the user will likely earn prior to retirement and an amount the user will save from the earnings for retirement. The system may view employment history of the user to determine a current salary of the user. Such employment history may include the occupation of the user. Additionally, the system may determine an expected increase in the salary of the user over a period of time prior to retirement. For example, the system may determine that the user is a teacher and paid a salary of $X.XX per annum. The user has been teaching for 5 years. The system may determine based on employment data that the salary of the user will increase 7% per year until the user retires. The system may determine an expected amount that the user will likely save for retirement from the increase in salary. In some embodiments, the system may determine that the user will receive benefits after retirement such as military and government benefits. These benefits will be included into a post-retirement income that will offset any amount the user may require to save for retirement.

In other embodiments, the system may determine that the user may want to partially retire and continue to receive an additional post-retirement income. In other embodiments, the system may further determine the user wants to start a business for retirement. The system may determine the amount of money the user needs to start the business and calculate the projected retirement score based on the needs to start the business. The system may further determine an expected salary from the business.

With respect to the amount of savings the user needs during retirement, the system may determine the cost of living for an area in which the user lives. Cost of living may include necessities such as groceries, rent, and insurance. Cost of living may also include other financial factors such as money for vacations, club memberships and such. In other embodiments, the system may determine based on past financial history of the user, the spending habits of the user to determine the amount the user needs during retirement. When the system determines past spending habits, the system may further determine whether the user plans to live a similar life style to which the user has lived prior to retirement. Such information may be gathered as a result of sending a questionnaire to the user. The information may further be received from a third-party consultant of the user (e.g. financial planner). In one example, the system may determine that the user has a property worth $X.XX amount of dollars which the user uses a primary residence. The system petitions the user whether the user intends to retain the property as a retirement home. If the user answers that the user intends to sell the property and rent a smaller property, the system would calculate the amount from a sale of the property and the amount the user would need for rent. The system may also determine insurance for the user during retirement. When the system determines that the user will receive a post-retirement income, the system may use such income to determine the amount the user needs to save after retirement.

With respect to amount of time the user has to save for retirement, the system may determine the current age of the user and the age at which the user would like to retire or partially retire. In other embodiments, the projected retirement score may include an age of retirement for a given score. For example, after the system receives the user profile and determines an amount the user would need for retirement, the system may determine different retirement ages for the user. The ages may be determined arbitrarily (e.g. the age of the user ten years in the future up until the user is a certain age), or the ages may be supplied by the user. After the retirement ages have been determined, the system may further calculate a projected retirement score for each age. For example, the user may supply a retirement age of 40, 45, 50, 55, and 60. Based on the both the amount the user has saved for retirement and the need of the user during retirement, the system may determine the projected retirement score for each age. Such score determines the readiness of the user to retire when the given age is achieved. In another embodiment, the projected retirement score is an age at which the user may retire.

In other embodiments, the system may determine different factors that may lower the projected retirement score of the user based on the financial information. Such factors may include paying off a higher interest loan faster or consolidating debt. The system may calculate a possible projected retirement score if the user corrects the factors. Additionally, the system may receive an indication that the user fulfilled the factors and update the projected retirement score accordingly.

At block 825, the system may be configured to determine a projected group retirement score range for the social network group. In some embodiments, the system is configured to receive from a manager of the social network group the projected group retirement score range. To receive the projected group retirement score range from the manager of the social network group, the system may be configured to present a form, via a computing device, to the manager for entering in the projected group retirement score range. After the manager enters the projected group retirement score range, the system communicates with the computing device to receive the projected group retirement score range. In another embodiment, the system is configured to calculate the projected group retirement score range. The system may calculate the projected group retirement score range based on financial information of the members in the social network group and more specifically based on a projected retirement score for each member of the group. Based on these scores, the system may determine the projected group retirement score range. For example, the system may determine both the maximum score of the group and the minimum score of the group and associate these scores with the projected group retirement score range. In another example, the system may use statistical analysis to determine the projected group retirement score range. While in another embodiment, the system may determine the projected group retirement score range in relation to the projected group retirement score range of a number of related social network groups. For example, the system may setup multiple social network groups to cover a projected retirement score range from 0 to 1000. The system may set the projected group retirement score range for each group to cover the entire range. In some embodiments, the range of one social network group may overlap the range of another social network group. For example, a first social network group may have a projected group retirement score range from 500-650, while a second social network group may have a projected retirement score range from 600-750.

Where the system is configured to calculate a confidence score, as defined herein, the system may be configured to calculate the confidence score of the social network group based on the information related to each member of the group. In some embodiments, the group confidence score may be based on individual confidence scores of each of the members of the group.

At block 830, the system may be configured to determine that the projected retirement score of the user is within the projected retirement score range for the social network group. And based at least in part on determining the projected retirement score of the user is within the projected retirement score range for the social network group, the system may be configured to create a group membership for the user to join the social network group as defined at block 835. In other embodiments, the system may be configured to generate the membership based on determining whether the user meets additional limitations for being admitted to the social network group as explained in block 805. For example, a social network group may have a limitation that permits membership based on whether a user is invested in a particular investment vehicle. In another example, the social network group may have a limitation that permits membership based on a particular age of the user. While in another example, the social network group may have a limitation that permits membership based on the employment of the user (e.g. employer, profession).

At block 840, embodiments of the invention further include demonstrates communicating the projected retirement score. The system may communicate the projected retirement score to a computing device of the user.

In some embodiments, after the system has created the membership for the user to join the social network group, the system may continue to receive information for the user in order to update the projected retirement score of the user.

Based on updating the projected retirement score of the user, the system may determine that such a score is not within the projected group retirement score range of the social network group. The system may determine a new social network group where the projected retirement score of the user is within a projected group retirement score range of the social network group. The system may then send the user an invitation to join the new social network group.

In this embodiment, the user is encouraged to increase the projected retirement score in order to be admitted into other groups. In some embodiments, the groups may be formed into tiers (e.g. bronze, silver gold). Each group may contain advantages to members of the group. An example of an advantage may access to a given financial product. Each group would have an admission requirement, which could be a given projected retirement score. As the user increases the projected retirement score, the system may be configured to admit the user into the subsequent social network groups.

In other embodiments, the system may further determine based on the financial information and the projected retirement score of the user, a mentor. The mentor may be a member of the same social network group of which the user is a member. Additionally, the mentor may be a member of a higher tiered group. In some embodiments, the system may recommend the mentor to the user based on the financial information of the user and the financial information of the mentor. The system may be configured to take a financial snap shot of the user and mentor for a given period of time. The system may determine that the financial information of the user is similar to a previous snap shot of the mentor. In this manner, the mentor could provide detailed strategy on how to help the user because the mentor was once where the user currently is.

The system may receive additional information about the members of the group which may include investment information. The system may determine different investment vehicles in which different group members are invested. The system may communicate a message to the user based on such a determination. For example, multiple members of the group may be invested in Stock A. The system may receive information that Stock A has increased in value. Based on such information, the system may communicate a message to the user giving information about Stock A. In other embodiments, the system may determine that members of the group are buying or selling different investment vehicles and communicate such information to the user.

The system may also be configured to create a communication link between the user and at least one other member of the group. The system may further be configured to allow the user to share the projected retirement score of the user to the at least one other member of the group and other financial information.

In other embodiments, the system may be configured to determine that a member of the group has increased an individual projected retirement score of the member. The system may review the financial information of the member to determine the reason for the increase in the projected retirement score of the member. The system may communicate a message to the user which includes the reason for the increase of the increase of the projected retirement score of the user.

In other embodiments, the system may offer a financial product to the user to increase the projected retirement score of the user. For example, the system may determine that the user does not save enough money and based on such determination generate and communicate an offer to the user to open a savings account with automatic transfer from a checking account to the savings account.

FIG. 9 illustrates a high level process flow for assessing retirement planning based on a retirement score and a market event 900. At block 902, the process flow comprises accessing the assets and the liabilities of a user over a network of servers, wherein the assets include illiquid assets and liquid assets, wherein the assets and the liabilities comprise a balance sheet. At block 904, the process flow comprises determining asset values and liability values. At block 906, the process flow comprises determining a retirement score based on the asset values and the liability values. At block 908, the process flow comprises determining a market event (e.g., an economic event, a stock or bond market event such as a loss of points greater than a threshold number on an index, a non-economic event, or the like). At block 910, the process flow comprises determining an increase or decrease in the retirement score based on the market event. Therefore, the present invention provides the user with a window into the user's predicted assets and liabilities following a market event. In some embodiments, the user is provided with a window into the user's social network. As used herein, a social network refers to users similarly situated to the user (e.g., similar asset and liability values). These users may or may not be directly connected to the user on a social network. The user is provided with a window into how these similarly situated users' retirement scores are affected following a market event. Therefore, the user may compare and contrast how the user's retirement score is affected versus how the other users' retirement scores are affected. The user may also receive advice on how to improve the user's performance (e.g., how to prevent a substantial drop in retirement score) based on the market event. To this effect, the user may be provided with a window into how similarly situated users are investing their assets or paying off their obligations. Therefore, the user may be able to modify the user's investment plan based on how similarly situated users are making investments and/or paying off their obligations.

In some embodiments, the balance sheet is presented on a graphical user interface. The graphical user interface enables a user to move funds in and out of the assets and/or liabilities list, and determine how the movement of the funds affects the user's ability to pay off certain obligations (or liabilities) or the user's ability to invest at least a portion of the assets in an investment plan. The investment plan comprises a plan for investing in stocks and bonds and may be presented on a graphical user interface. In some embodiments, the investment plan may also be based on a market event. Additionally, the invention described herein picks stocks and bonds based on the retirement score and/or the physical health score and/or the market event. For example, the invention described picks higher growth stocks (and lower market capitalization stocks) and higher-yielding bonds if the retirement score is greater than a threshold score, and picks lower growth stocks (and higher market capitalization stocks) and lower-yielding bonds if the retirement score is less than the threshold score. The growth stocks may refer to at least one of growth in revenue, growth in earnings per share, and/or growth in share price. In some embodiments, the investment plan comprises an investment plan for investing in other types of assets (e.g., real property, art work, or the like). The investment plan may also provide a plan for converting some of the liquid assets into illiquid assets (e.g., if the user is obtain a higher income interest rate on the illiquid assets compared to the liquid assets), or converting some of the illiquid assets into liquid assets (e.g., if any of the liabilities have due dates that are approaching in the near future) based on the retirement score and/or the market event. In some embodiments, the process flow further comprises receiving a physical health score associated with the user, the retirement score being associated with the physical well-being of the user, wherein the investment plan is further based on the physical health score. Therefore, the types of investment plans and obligation payoff plans may be based on the physical health score.

FIG. 10 illustrates a high level process flow for determining a projected retirement score 1000. As shown in block 1005, embodiments of the invention further include user health information. This information may both include health related factors and non-health related factors. With respect to non-health related factors, determining life expectancy may include the demography of the user and the occupation of the user.

With respect to health related factors, life expectancy may take into account the physical fitness of the user, genetics, currently known diseases or disorders, and other risk factors. With respect to the physical fitness of the user, factors may include determining the weight of the user, the amount the user exercises, and the age of the user. With respect to genetics, factors may include risk of acquiring a disease based on family medical history. Other risk factors may include factors that have been known to have an impact on a life expectancy of a person such as whether and how much the user smokes, whether and how much the user drinks, whether the user takes any medications, and such.

As described in block 1010, the system may be configured to determine a life expectancy of the user. In some embodiments, determining the life expectancy of the user may be performed using standard calculations, such as when determining life expectancy for life insurance policies. Life expectancy may be based both on health related factors and non-health related factors.

As described in block 1015, the system may determine projected allocations of finances for health care of the user. Such information may include any treatments the user is expected to have during the lifetime of the member and additionally when the user retires. Additionally, the information may also include prescriptions that the user is likely to have.

As described in block 1020, the system may be configured to receive retirement information of the user. The retirement information may relate to assets and liabilities of the user, wherein the assets include illiquid assets and liquid assets. The user's assets may include but are not limited to checking accounts, savings accounts, investment accounts (e.g., with regular disbursements and penalties for principal withdrawals, or self-directed accounts that more liquid without penalties), annuity accounts (e.g., social security, claim awards, reverse mortgages, or the like), insurances benefit accounts (e.g., one time or reoccurring), property owned by the user (e.g., investment property, rental property, or the like), or other like assets that may provide regular or semi-regular recurring payments, assets that are or are similar to cash accounts, or assets that need to be sold in order to realize cash values of the assets. In some embodiments the assets may be illiquid (e.g., have penalties or may take time to convert into cash) or may be liquid (e.g., can be converted to cash in a couple of days without penalty). In one aspect, the process flow includes determining a user's asset values (e.g., balances of the account, current or estimated future fair market values of the property, or the like) and liability values (e.g., amount owed, or the like). The user's liabilities may include a mortgage, long and short term debit, payments owed on other personal property or legal judgments against the user, or the like). In some embodiments all of the assets and liabilities are determined in order to get an idea of what the values of the assets and liabilities are in order to determine how long the inflows and outflows for the user may last. In one aspect, the retirement information may further include at least information identifying the user.

At block 1025, embodiments of the invention further include generating a projected retirement score based on the projected retirement information of the user. In some embodiments, the system calculates the projected retirement score based at least in part on an amount of savings of the user for retirement, an amount of savings the user needs during retirement, and a number of years the user has to get ready for retirement. With respect to the amount of savings of the user for retirement, the system may identify savings and other retirement accounts from the user. The system may automatically determine a retirement account based on the type of account (e.g. 401K). In other embodiments, the user may designate an account as a retirement account. Where the account is an interest bearing account, the system may calculate at least a future amount based on the system collecting and compounding interest. For example, the user may have designated a savings account as a retirement account that generates 1% per annum. The system further determines that the user contributes $100 per month into the savings account. The system may determine an available amount of funds at a future period of time based on such information. The future period of time may coincide with the retirement of the user. Where the account is an investment account, the system may determine based on market information, an amount each investment vehicle in account will be worth at a future period of time. In addition to account information, the system may determine that the user maintains an interest of ownership in real property. With respect to the user's ownership in real property, the system may determine based on historic market information of the property, a value of the property at a future period of time. The system may further determine whether the property generates an income (e.g. rent, timber sale, farm product). The system may valuate the land based on the generated income of the property. In other embodiments, the system may determine an amount the user will likely earn prior to retirement and an amount the user will save from the earnings for retirement. The system may view employment history of the user to determine a current salary of the user. Such employment history may include the occupation of the user. Additionally, the system may determine an expected increase in the salary of the user over a period of time prior to retirement. For example, the system may determine that the user is a teacher and paid a salary of $X.XX per annum. The user has been teaching for 5 years. The system may determine based on employment data that the salary of the user will increase 7% per year until the user retires. The system may determine an expected amount that the user will likely save for retirement from the increase in salary. In some embodiments, the system may determine that the user will receive benefits after retirement such as military and government benefits. These benefits will be included into a post-retirement income that will offset any amount the user may require to save for retirement.

In other embodiments, the system may determine that the user may want to partially retire and continue to receive an additional post-retirement income. In other embodiments, the system may further determine the user wants to start a business for retirement. The system may determine the amount of money the user needs to start the business and calculate the projected retirement score based on the needs to start the business. The system may further determine an expected salary from the business.

With respect to the amount of savings the user needs during retirement, the system may determine the cost of living for an area in which the user lives. Cost of living may include necessities such as groceries, rent, and insurance. Cost of living may also include other financial factors such as money for vacations, club memberships and such. In other embodiments, the system may determine based on past financial history of the user, the spending habits of the user to determine the amount the user needs during retirement. When the system determines past spending habits, the system may further determine whether the user plans to live a similar life style to which the user has lived prior to retirement. Such information may be gathered as a result of sending a questionnaire to the user. The information may further be received from a third-party consultant of the user (e.g. financial planner). In one example, the system may determine that the user has a property worth $X.XX amount of dollars which the user uses a primary residence. The system petitions the user whether the user intends to retain the property as a retirement home. If the user answers that the user intends to sell the property and rent a smaller property, the system would calculate the amount from a sale of the property and the amount the user would need for rent. The system may also determine insurance for the user during retirement. When the system determines that the user will receive a post-retirement income, the system may use such income to determine the amount the user needs to save after retirement.

With respect to amount of time the user has to save for retirement, the system may determine the current age of the user and the age at which the user would like to retire or partially retire. In other embodiments, the projected retirement score may include an age of retirement for a given score. For example, after the system determines an amount the user would need for retirement, the system may determine different retirement ages for the user. The ages may be determined arbitrarily (e.g. the age of the user ten years in the future up until the user is a certain age), or the ages may be supplied by the user. After the retirement ages have been determined, the system may further calculate a projected retirement score for each age. For example, the user may supply a retirement age of 40, 45, 50, 55, and 60. Based on the both the amount the user has saved for retirement and the need of the user during retirement, the system may determine the projected retirement score for each age. Such score determines the readiness of the user to retire when the given age is achieved. In another embodiment, the projected retirement score is an age at which the user may retire.

In other embodiments, the system may determine different factors that may lower the projected retirement score of the user based on the financial information. Such factors may include paying off a higher interest loan faster or consolidating debt. The system may calculate a possible projected retirement score if the user corrects the factors. Additionally, the system may receive an indication that the user fulfilled the factors and update the projected retirement score accordingly.

In other embodiments, the system may further determine the projected retirement score based on the health information of the user. The system may determine expenses that the user will likely incur during retirement based on the health information. For example, if the user is expected to be prescribed a given prescription during retirement, the system may determine the cost of such prescription and calculate the projected retirement score appropriately.

As described in block 1030, the system may be configured to communicate the projected retirement score. The system may communicate the projected retirement score to a computing device of the user.

After the system determines the life expectancy and projected retirement score, the system may continue to receive both health and retirement information to update both the life expectancy and the projected retirement score of the user.

In some embodiments, the system may communicate with a fitness tracker of the user to determine the level of fitness activity of the user. The fitness tracker may include a pedometer, a weight scale, a sleep monitor, health rate monitor, a blood analyzer, or another medical device. In some embodiments, the system connects directly to the fitness tracker in order to receive the health related information for the user. In other embodiments, the fitness tracker may connect to the system using an intermediary device such as a mobile device of the user. For example, the fitness tracker may have a short range communication device installed and connects to the mobile device of the user using the short range communication device. The mobile device may be able to connect either directly or indirectly to the system over a common network. Based on the fitness information that the system receives, the system may update the life expectancy of the user and the projected retirement score of the user. In some embodiments, the system may determine that the user has been inactive for a given period of time and send a reminder to the user to perform a physical activity such as walking for 10 minutes. The system may determine the user has been inactive based on information collected from the fitness tracker. For example, where the fitness tracker is a pedometer, the fitness tracker may track the number of steps of consecutive periods of time (e.g. every hour). The fitness tracker may communicate every hour the number of steps taken by the user for each hour. The system may be configured to determine that if a user does not take a predetermined number of steps within the hour, the system may communicate the message to the user. In some embodiments, the system may communicate the message to the user by sending a request to the fitness tracker. For example, where the fitness tracker includes a display, the system may cause the fitness tracker to display the information via the display of the fitness tracker. In other embodiments, the system may cause the fitness tracker to vibrate. In other embodiments, the system may communicate the updated life expectancy and the updated projected retirement score to the fitness tracker.

In other embodiments, the system may determine healthy activities to communicate to the user. Such activity may include a fitness activity such as jogging or walking up the stairs. In other embodiments, the system may determine the location of the user. Such determination may be performed using a mobile device of the user or the fitness tracker of the user. The system may cause the mobile device or fitness tracker to determine the location of the user. The system may then receive the location of the user. Based on the location information, the system may determine restaurants in the area that serve healthy meals. The system may communicate a message to the user that includes the healthy meal option. In some embodiments, the message may include an offer from the restaurant. In other embodiments, the system may determine that the user is located at a grocery store. The system may determine that the store offers healthy foods. The system may generate and communicate an offer to the user for the healthy foods offered by the grocery store. Such offers may be based on the financial history of the user. In yet other embodiments, the system may determine that the user is proximately located to a fitness center. The system may receive financial information of the user and determine based on the financial information that the user is not a member of a financial institution. The system may notify the user of the location of the fitness center and provide an offer to the user to join the fitness center.

After the system has communicated a fitness activity to the user, the system may receive an indication that the user has completed the activity. Based on receiving the indication that the user has completed the activity, the system may update the life expectancy of the user and the projected retirement score of the user.

In other embodiments, the system may be configured to allow the user to set fitness goals. The system may receive information that the user has completed a goal and based on such information update the life expectancy and the projected retirement goal of the user.

In other embodiments, when the system calculates a change in the life expectancy of the user and the projected retirement score of the user, the system may receive insurance information of the user. Based on such information the system may determine an insurance provider (e.g. health, life) that covers the user. The system may communicate the updated life expectancy and the updated projected retirement score of the user to the insurance provider in order to negotiate for better terms of the insurance policy.

In some embodiments, the system may be configured to present a dashboard to the user containing the health information of the user. The dashboard may contain various activities that could affect the projected retirement score of the user. These activities may include exercise habits and eating habits. The system may associate with each activity a change in the projected retirement score. For example, the dashboard may present an activity for the user to jog 15 minutes every day for a year and suggest that the projected retirement score may increase by 15 points. Alternatively, the dashboard may also present activities that would lower the projected retirement score of the user. The system may enable the user to select that at least one of the activities presented via the dashboard has been completed. After receiving such a selection, the system may be configured to update the projected retirement score. In some embodiments, the system may enable the user to report on different activities on a periodic basis (e.g. daily, monthly). For example, the system may receive information related to the diet of the user. Based on the diet information, the system may update the projected retirement score.

FIG. 11 illustrates a high level process flow for assessing retirement planning based on a retirement score and investments associated with the user 1100. At block 1102, the process flow comprises accessing the assets and the liabilities of a user over a network of servers, wherein the assets include illiquid assets and liquid assets, wherein the assets and the liabilities comprise a balance sheet. At block 1104, the process flow comprises determining asset values and liability values. At block 1106, the process flow comprises determining a retirement score based on the asset values and the liability values. At block 1108, the process flow comprises in response to determining the retirement score is equal to or greater than a threshold score, provide a first recommendation to the user, the first recommendation comprising an investment plan for at least a portion of the liquid assets.

In some embodiments, the balance sheet is presented on a graphical user interface. The graphical user interface enables a user to move funds in and out of the assets and/or liabilities list, and determine how the movement of the funds affects the user's ability to pay off certain obligations (or liabilities) or the user's ability to invest at least a portion of the assets in an investment plan. The investment plan comprises a plan for investing in stocks and bonds and may be presented on a graphical user interface. Additionally, the invention described herein picks stocks and bonds based on the retirement score and/or the physical health score described below. For example, the invention described picks higher growth stocks (and lower market capitalization stocks) and higher-yielding bonds if the retirement score is greater than a threshold score, and picks lower growth stocks (and higher market capitalization stocks) and lower-yielding bonds if the retirement score is less than the threshold score. The growth stocks may refer to at least one of growth in revenue, growth in earnings per share, and/or growth in share price. In some embodiments, the investment plan comprises an investment plan for investing in other types of assets (e.g., real property, art work, or the like). The investment plan may also provide a plan for converting some of the liquid assets into illiquid assets (e.g., if the user is obtain a higher income interest rate on the illiquid assets compared to the liquid assets), or converting some of the illiquid assets into liquid assets (e.g., if any of the liabilities have due dates that are approaching in the near future). In some embodiments, the system indicates a confidence level associated with matching the user to other users (e.g., on the user's social network). If the confidence level is higher (e.g., greater than a threshold level), a recommendation may be provided to the user to alter the user's investment plan or payoff plan based on the other users' plans. In some embodiments, the type of investment plan or payoff plan is also based on the user's tolerance either defined by the user or defined for the user based on other information associated with the user as described herein.

In some embodiments, the process flow further comprises in response to determining the retirement score is less than the threshold score, providing a second recommendation to the user, the second recommendation comprising a payoff plan for paying off at least a portion of the liabilities (or obligations) using at least one of the illiquid assets or the liquid assets. In some embodiments, the process flow further comprises receiving a physical health score associated with the user, the retirement score being associated with the physical well-being of the user, wherein the investment plan is further based on the physical health score. Therefore, the types of investment plans and obligation payoff plans may be based on the physical health score.

In accordance with embodiments of the invention, the term "module" with respect to a system may refer to a hardware component of the system, a software component of the system, or a component of the system that includes both hardware and software. As used herein, a module may include one or more modules, where each module may reside in separate pieces of hardware or software.

Although many embodiments of the present invention have just been described above, the present invention may be embodied in many different forms and should not be construed as limited to the embodiments set forth herein; rather, these embodiments are provided so that this disclosure will satisfy applicable legal requirements. Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. Accordingly, the terms "a" and/or "an" shall mean "one or more," even though the phrase "one or more" is also used herein. Like numbers refer to like elements throughout.

As will be appreciated by one of ordinary skill in the art in view of this disclosure, the present invention may include and/or be embodied as an apparatus (including, for example, a system, machine, device, computer program product, and/or the like), as a method (including, for example, a business method, computer-implemented process, and/or the like), or as any combination of the foregoing. Accordingly, embodiments of the present invention may take the form of an entirely business method embodiment, an entirely software embodiment (including firmware, resident software, micro-code, stored procedures in a database, or the like), an entirely hardware embodiment, or an embodiment combining business method, software, and hardware aspects that may generally be referred to herein as a "system." Furthermore, embodiments of the present invention may take the form of a computer program product that includes a computer-readable storage medium having one or more computer-executable program code portions stored therein. As used herein, a processor, which may include one or more processors, may be "configured to" perform a certain function in a variety of ways, including, for example, by having one or more general-purpose circuits perform the function by executing one or more computer-executable program code portions embodied in a computer-readable medium, and/or by having one or more application-specific circuits perform the function.

It will be understood that any suitable computer-readable medium may be utilized. The computer-readable medium may include, but is not limited to, a non-transitory computer-readable medium, such as a tangible electronic, magnetic, optical, electromagnetic, infrared, and/or semiconductor system, device, and/or other apparatus. For example, in some embodiments, the non-transitory computer-readable medium includes a tangible medium such as a portable computer diskette, a hard disk, a random access memory (RAM), a read-only memory (ROM), an erasable programmable read-only memory (EPROM or Flash memory), a compact disc read-only memory (CD-ROM), and/or some other tangible optical and/or magnetic storage device. In other embodiments of the present invention, however, the computer-readable medium may be transitory, such as, for example, a propagation signal including computer-executable program code portions embodied therein.

One or more computer-executable program code portions for carrying out operations of the present invention may include object-oriented, scripted, and/or unscripted programming languages, such as, for example, Java, Perl, Smalltalk, C++, SAS, SQL, Python, Objective C, JavaScript, and/or the like. In some embodiments, the one or more computer-executable program code portions for carrying out operations of embodiments of the present invention are written in conventional procedural programming languages, such as the "C" programming languages and/or similar programming languages. The computer program code may alternatively or additionally be written in one or more multi-paradigm programming languages, such as, for example, F#.

Some embodiments of the present invention are described herein with reference to flowchart illustrations and/or block diagrams of apparatus and/or methods. It will be understood that each block included in the flowchart illustrations and/or block diagrams, and/or combinations of blocks included in the flowchart illustrations and/or block diagrams, may be implemented by one or more computer-executable program code portions. These one or more computer-executable program code portions may be provided to a processor of a general purpose computer, special purpose computer, and/or some other programmable data processing apparatus in order to produce a particular machine, such that the one or more computer-executable program code portions, which execute via the processor of the computer and/or other programmable data processing apparatus, create mechanisms for implementing the steps and/or functions represented by the flowchart(s) and/or block diagram block(s).

The one or more computer-executable program code portions may be stored in a transitory and/or non-transitory computer-readable medium (e.g. a memory) that can direct, instruct, and/or cause a computer and/or other programmable data processing apparatus to function in a particular manner, such that the computer-executable program code portions stored in the computer-readable medium produce an article of manufacture including instruction mechanisms which implement the steps and/or functions specified in the flowchart(s) and/or block diagram block(s).

The one or more computer-executable program code portions may also be loaded onto a computer and/or other programmable data processing apparatus to cause a series of operational steps to be performed on the computer and/or other programmable apparatus. In some embodiments, this produces a computer-implemented process such that the one or more computer-executable program code portions which execute on the computer and/or other programmable apparatus provide operational steps to implement the steps specified in the flowchart(s) and/or the functions specified in the block diagram block(s). Alternatively, computer-implemented steps may be combined with, and/or replaced with, operator- and/or human-implemented steps in order to carry out an embodiment of the present invention.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other changes, combinations, omissions, modifications and substitutions, in addition to those set forth in the above paragraphs, are possible. Those skilled in the art will appreciate that various adaptations, modifications, and combinations of the just described embodiments can be configured without departing from the scope and spirit of the invention. Therefore, it is to be understood that, within the scope of the appended claims, the invention may be practiced other than as specifically described herein.

What is claimed is:

1. A system for determining a projected retirement score, the system comprising:
   a memory;
   a communication device connected to a distributed network;
   a processing device;
   a software module stored in memory comprising executable instructions that when executed by the processing device, cause the processing device to:
      compile into a structured database connected to the distributed network projected retirement information of a first user, wherein the projected retirement information comprises a user profile of the first user;
      generate a projected retirement score based on the projected retirement information of the first user, wherein the projected retirement score is an estimate of the first user's preparedness for retirement at a future predetermined date, wherein the projected retirement information comprises a life expectancy of the first user;
      establish a connection with a fitness tracker of the first user;
      cause the fitness tracker to determine a location of the first user;
      receive the location of the first user from the fitness tracker;
      determine a fitness activity based on the location of the first user;
      prompt the first user to perform the fitness activity by causing the fitness tracker to display a message and causing the fitness tracker to vibrate;
      determine that the first user has completed the fitness activity;
      update the life expectancy of the first user and the projected retirement score based on determining that the first user has completed the fitness activity;
      receive, from a personal computing device connected to the distributed network, a request to link a user profile for a second user to the user profile of the first user;
      authorize the request to link the user profile of the second user with the user profile of the first user based at least in part on an association between the first user and the second user;
      compile, into the structured database, projected retirement information of the second user based on authorizing the request to link the user profile of the second user to the user profile of the first user;
      combine the projected retirement information of the first user with the projected retirement information of the second user, thus resulting in combined projected retirement information;
      further update the projected retirement score based on the combined projected retirement information; and
      communicate to the personal computing device, via the communication device, the projected retirement score.

2. The system of claim 1, wherein the software module further comprises instructions that cause the processing device to:
   determine an expected age of retirement of at least the first user and the second user;
   determine a number of years before the first user retires based on the expected age of retirement of the first user;
   determine a number of years before the second user retires based on the expected age of retirement of the second user;
   wherein, generating the projected retirement score is further based on the number of years before the first user retires; and
   wherein, further updating the projected retirement score is further based on the number of years before the second user retires.

3. The system of claim 1, wherein the software module further comprises an instruction that causes the processing device to receive payment information for future payments of the first user or the second user, wherein, generating the projected retirement score is further based on the future payments of the first user, and wherein, further updating the projected retirement score is further based on the future payments of the second user.

4. The system of claim 1, wherein the software module further comprises an instruction that causes the processing device to determine a difference between the generated projected retirement score and the further updated projected retirement score, and communicate to the personal computing device, via the communication device, the difference between the generated projected retirement score and the further updated projected retirement score.

5. The system of claim 1, wherein the software module further comprises an instruction that causes the processing device to determine an expected increase in earnings of the first user and the second user, wherein generating the projected retirement score is further based on the expected increase in earning of the first user, and wherein, further updating the projected retirement score is further based on the expected increase in earning of the second user.

6. The system of claim 5, wherein the expected increase in earnings comprises expected funds from retirement programs.

7. The system of claim 1, wherein the retirement information comprises at least financial account information, retirement account information.

8. A method for determining a projected retirement score, comprising:
 compiling into a structured database connected to a distributed network projected retirement information of a first user, wherein the projected retirement information comprises a user profile of the first user;
 generating a projected retirement score based on the projected retirement information of the first user, wherein the projected retirement score is an estimate of the first user's preparedness for retirement at a future predetermined date, wherein the projected retirement information comprises a life expectancy of the first user;
 establishing a connection with a fitness tracker of the first user;
 causing the fitness tracker to determine a location of the first user;
 receiving the location of the first user from the fitness tracker;
 determining a fitness activity based on the location of the first user;
 prompting the first user to perform the fitness activity by causing the fitness tracker to display a message and causing the fitness tracker to vibrate;
 determining that the first user has completed the fitness activity;
 updating the life expectancy of the first user and the projected retirement score based on determining that the first user has completed the fitness activity;
 receiving from a personal computing device connected to the distributed network, a request to link a user profile for a second user to the user profile of the first user;
 authorizing the request to link the user profile of the second user with the user profile of the first user based at least in part on an association between the first user and the second user;
 compiling into the structured database projected retirement information of the second user based on authorizing the request to link the user profile of the second user to the user profile of the first user;
 combining the projected retirement information of the first user with the projected retirement information of the second user, thus resulting in combined projected retirement information;
 further updating the projected retirement score based on the combined projected retirement information; and
 communicating to the personal computing device, via a communication device, the projected retirement score.

9. A computer program product for determining a projected retirement score comprising a non-transitory computer-readable storage medium having computer-executable instructions to:
 compile into a structured database connected to a distributed network projected retirement information of a first user, wherein the projected retirement information comprises a user profile of the first user;
 generate a projected retirement score based on the projected retirement information of the first user, wherein the projected retirement score is an estimate of the first user's preparedness for retirement at a future predetermined date, wherein the projected retirement information comprises a life expectancy of the first user;
 establish a connection with a fitness tracker of the first user;
 cause the fitness tracker to determine a location of the first user;
 receive the location of the first user from the fitness tracker;
 determine a fitness activity based on the location of the first user;
 prompt the first user to perform the fitness activity by causing the fitness tracker to display a message and causing the fitness tracker to vibrate;
 determine that the first user has completed the fitness activity;
 update the life expectancy of the first user and the projected retirement score based on determining that the first user has completed the fitness activity;
 receive from a personal computing device connected to the distributed network, a request to link a user profile for a second user to the user profile of the first user;
 authorize the request to link the user profile of the second user with the user profile of the first user based at least in part on an association between the first user and the second user;
 compile into the structured database projected retirement information of the second user based on authorizing the request to link the user profile of the second user to the user profile of the first user;
 combine the projected retirement information of the first user with the projected retirement information of the second user, thus resulting in combined projected retirement information;
 further update the projected retirement score based on the combined projected retirement information; and
 communicate to the personal computing device, via a communication device, the projected retirement score.

10. The computer program product of claim 9, wherein the non-transitory computer-readable storage medium further having computer-executable instructions to:
 determine an expected age of retirement of at least the first user and the second user;
 determine a number of years before the first user retires the expected age of retirement of the first user;
 determine a number of years before the second user retires based on the expected age of retirement of the second user;

wherein, generating the projected retirement score is further based on the number of years before the first user retires; and wherein, further updating the projected retirement score is further based on the number of years before the second user retires.

11. The computer program product of claim 9, wherein the non-transitory computer-readable storage medium further having computer-executable instructions to receive payment information for future payments of the first user or the second user, wherein, generating the projected retirement score is further based on the future payments of the first user, and wherein, further updating the projected retirement score is further based on the future payments of the second user.

12. The computer program product of claim 9, wherein the non-transitory computer-readable storage medium further having computer-executable instructions to determine a difference between the generated projected retirement score and the further updated projected retirement score, and communicate to the personal computing device, via the communication device, the difference between the generated projected retirement score and the further updated projected retirement score.

13. The computer program product of claim 9, wherein the non-transitory computer-readable storage medium further having computer-executable instructions to determine an expected increase in earnings of the first user and the second user, wherein generating the projected retirement score is further based on the expected increase in earning of the first user, and wherein, further updating the projected retirement score is further based on the expected increase in earning of the second user.

14. The computer program product of claim 13, wherein the expected increase in earnings comprises expected funds from retirement programs.

15. The computer program product of claim 9, wherein the retirement information comprises at least financial account information, retirement account information.

16. The method of claim 8, the method further comprising determining a difference between the generated projected retirement score and the further updated projected retirement score, and communicating to the personal computing device, via the communication device, the difference between the generated projected retirement score and the further updated projected retirement score.

17. The method of claim 16, further comprising:
determining an expected age of retirement of at least the first user and the second user;
determining a number of years before the first user retires based on the expected age of retirement of the first user;
determining a number of years before the second user retires based on the expected age of retirement of the second user;
wherein, generating the projected retirement score is further based on the number of years before the first user retires; and
wherein, further updating the projected retirement score is further based on the number of years before the second user retires.

18. The method of claim 16, the method further comprising receiving payment information for future payments of the first user or the second user, wherein, generating the projected retirement score is further based on the future payments of the first user, and wherein, further updating the projected retirement score is further based on the future payments of the second user.

19. The method of claim 16, the method further comprising determining an expected increase in earnings of the first user and the second user, wherein generating the projected retirement score is further based on the expected increase in earning of the first user, and wherein, further updating the projected retirement score is further based on the expected increase in earning of the second user.

20. The method of claim 19, wherein the expected increase in earnings comprises expected funds from retirement programs.

* * * * *